United States Patent
Liu et al.

(10) Patent No.: US 10,633,658 B2
(45) Date of Patent: Apr. 28, 2020

(54) METHOD FOR PRODUCING N-ACETYLGLUCOSAMINE BY CO-UTILIZING GLUCOSE AND XYLOSE BASED ON CRISPRI

(71) Applicant: Jiangnan University, Wuxi (CN)

(72) Inventors: Long Liu, Wuxi (CN); Jian Chen, Wuxi (CN); Guocheng Du, Wuxi (CN); Jianghua Li, Wuxi (CN); Yaokang Wu, Wuxi (CN); Taichi Chen, Wuxi (CN)

(73) Assignee: JIANGNAN UNIVERSITY, Wuxi, Jiangsu (CN)

( * ) Notice: Subject to any disclaimer, the term of this patent is extended or adjusted under 35 U.S.C. 154(b) by 0 days.

(21) Appl. No.: 16/112,959

(22) Filed: Aug. 27, 2018

(65) Prior Publication Data

US 2019/0218548 A1 Jul. 18, 2019

(30) Foreign Application Priority Data

Jan. 15, 2018 (CN) .......................... 2018 1 0036701

(51) Int. Cl.
| | |
|---|---|
| *C12N 15/63* | (2006.01) |
| *C12N 15/113* | (2010.01) |
| *C12N 9/22* | (2006.01) |
| *C12P 19/02* | (2006.01) |

(52) U.S. Cl.
CPC .............. *C12N 15/113* (2013.01); *C12N 9/22* (2013.01); *C12P 19/02* (2013.01); *C12N 2310/14* (2013.01); *C12N 2310/20* (2017.05); *C12N 2500/34* (2013.01); *C12N 2510/02* (2013.01); *C12N 2800/80* (2013.01)

(58) Field of Classification Search
CPC ....... C12N 15/1082; C12N 15/63; C12N 1/20
See application file for complete search history.

(56) References Cited

PUBLICATIONS

Liu et al. 2014; Modular pathway engineering of Bacillus subtilis for improved N-acetylglucosamine production. Metabolic Engineering. 23: 42-52.*

* cited by examiner

*Primary Examiner* — Karen Cochrane Carlson
(74) *Attorney, Agent, or Firm* — IPro, PLLC; Na Xu

(57) ABSTRACT

The present invention discloses a method for producing N-acetylglucosamine (GlcNAc) by co-utilizing glucose and xylose based on CRISPRi, and belongs to the field of genetic engineering. According to the method, *Bacillus subtilis* BSGNY-$P_{veg}$-glmS-$P_{43}$-GNA1 is used as an original strain, dCas9 induced by xylose and three sgRNA expression fragments targeting to genes zwf, pfkA and glmM respectively are integrated on the genome, and the strain is fermented in a shake flask, so that the titer of GlcNAc reaches 20.5 g/L, the yield of GlcNAc is 0.612 g/g glucose, at the same time, the efficient co-utilizing of glucose and xylose by the recombinant *B.s subtilis* is achieved, and the foundation for further metabolic engineering transformation of the *B. subtilis* to produce GlcNAc and industrialization thereof is laid.

9 Claims, 5 Drawing Sheets

Specification includes a Sequence Listing.

SEQUENCE LISTING

```
<160> NUMBER OF SEQ ID NOS: 18

<210> SEQ ID NO 1
<211> LENGTH: 1368
<212> TYPE: PRT
<213> ORGANISM: Artificial Sequence
<220> FEATURE:
<223> OTHER INFORMATION: Protein translated from Synthetic DNA

<400> SEQUENCE: 1

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

-continued

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
```

```
               995                 1000                1005
Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 102
<212> TYPE: DNA
<213> ORGANISM: Artificial Sequence
```

```
<220> FEATURE:
<223> OTHER INFORMATION: Synthetic DNA

<400> SEQUENCE: 2
cgaagatcct cattagacca gttttagagc tagaaatagc aagttaaaat aaggctagtc    60
cgttatcaac ttgaaaaagt ggcaccgagt cggtgctttt tt                      102

<210> SEQ ID NO 3
<211> LENGTH: 102
<212> TYPE: DNA
<213> ORGANISM: Artificial Sequence
<220> FEATURE:
<223> OTHER INFORMATION: Synthetic DNA

<400> SEQUENCE: 3
ccgattgtaa aatcagtgcc gttttagagc tagaaatagc aagttaaaat aaggctagtc    60
cgttatcaac ttgaaaaagt ggcaccgagt cggtgctttt tt                      102

<210> SEQ ID NO 4
<211> LENGTH: 102
<212> TYPE: DNA
<213> ORGANISM: Artificial Sequence
<220> FEATURE:
<223> OTHER INFORMATION: Synthetic DNA

<400> SEQUENCE: 4
tatcctcagg ttcgtccatc gttttagagc tagaaatagc aagttaaaat aaggctagtc    60
cgttatcaac ttgaaaaagt ggcaccgagt cggtgctttt tt                      102

<210> SEQ ID NO 5
<211> LENGTH: 10363
<212> TYPE: DNA
<213> ORGANISM: Artificial Sequence
<220> FEATURE:
<223> OTHER INFORMATION: Synthetic DNA

<400> SEQUENCE: 5
tcgagttcat gtgcagctcc atcagcaaaa ggggatgata agtttatcac caccgactat    60
ttgcaacagt gccgttgatc gtgctatgat cgactgatgt catcagcggt ggagtgcaat   120
gtcatgaggg aagcggtgat cgccgaagta tcgactcaac tatcagaggt agttggcgtc   180
atcgagcgcc atctcgaacc gacgttgctg gccgtacatt tgtacggctc cgcagtggat   240
ggcggcctga agccacacag tgatattgat ttgctggtta cggtgaccgt aaggcttgat   300
gaaacaacgc ggcgagcttt gatcaacgac cttttgaaa cttcggcttc ccctggagag   360
agcgagattc tccgcgctgt agaagtcacc attgttgtgc acgacgacat cattccgtgg   420
cgttatccag ctaagcgcga actgcaattt ggagaatggc agcgcaatga cattcttgca   480
ggtatcttcg agccagccac gatcgacatt gatctggcta tcttgctgac aaaagcaaga   540
gaacatagcg ttgccttggt aggtccagcg gcggaggaac tctttgatcc ggttcctgaa   600
caggatctat ttgaggcgct aaatgaaacc ttaacgctat ggaactcgcc gcccgactgg   660
gctggcgatg agcgaaatgt agtgcttacg ttgtcccgca tttggtacag cgcagtaacc   720
ggcaaaatcg cgccgaagga tgtcgctgcc gactgggcaa tggagcgcct gccggcccag   780
tatcagcccg tcatacttga agctagacag gcttatcttg acaagaaga agatcgcttg   840 gcctcgcgcg cagatcagtt ggaagaattt gtccactacg tgaaaggcga gatcaccaag   900
gtagtcggca aataagatgc cgctcgccag tcgattggct gagctcatga agttcctatt   960
```

```
ccgaagttcc gcgaacgcgt aaaggatcta ggtgaagatc cttttttgata atctcatgac    1020 caaaatccct taacgtgagt tttcgttcca ctgagcgtca gacccgtag aaaagatcaa      1080 aggatcttct tgagatcctt tttttctgcg cgtaatctgc tgcttgcaaa caaaaaaacc    1140
accgctacca gcggtggttt gtttgccgga tcaagagcta ccaactcttt ttccgaaggt    1200
aactggcttc agcagagcgc agataccaaa tactgtcctt ctagtgtagc cgtagttagg    1260
ccaccacttc aagaactctg tagcaccgcc tacatacctc gctctgctaa tcctgttacc    1320
agtggctgct gccagtggcg ataagtcgtg tcttaccggg ttggactcaa gacgatagtt    1380
accggataag gcgcagcggt cgggctgaac ggggggttcg tgcacacagc ccagcttgga    1440
gcgaacgacc tacaccgaac tgagatacct acagcgtgag ctatgagaaa gcgccacgct    1500
tcccgaaggg agaaaggcgg acaggtatcc ggtaagcggc agggtcggaa caggagagcg    1560
cacgagggag cttccagggg gaaacgcctg gtatctttat agtcctgtcg ggtttcgcca    1620
cctctgactt gagcgtcgat ttttgtgatg ctcgtcaggg gggcggagcc tatggaaaaa    1680
cgccagcaac gcggccttttt tacggttcct ggccttttgc tggccttttg ctcacatgtt    1740
ctttcctgcg ttatcccctg attctgtgga taaccgtatt accgcctttg agtgagctga    1800
taccgctcgc cgcagccgaa cgaccgagcg cagcgagtca gtgagcgagg aagcggaaga    1860
gcgcctgatg cggtatttttc tccttacggg aattccatat ggattccgtg atgtcaaagc    1920
ttgaaaaaac gcacgtaaca aaagcaaaat ttatgctcca tgggggagac tacaaccccg    1980
atcagtggct ggatcggccc gatattttag ctgacgatat caaactgatg aagctttctc    2040
atacgaatac gttttctgtc ggcattttttg catggagcgc acttgagccg gaggagggcg    2100
tatatcaatt tgaatggctg gatgatatttt ttgagcggat tcacagtata ggcggccggg    2160
tcatattagc aacgccgagc ggagcccgtc cggcctggct gtcgcaaacc tatccggaag    2220
ttttgcgcgt caatgcctcc cgcgtcaaac agctgcacgg cggaaggcac aaccactgcc    2280
tcacatctaa agtctaccga gaaaaaacac ggcacatcaa ccgcttatta gcagaacgat    2340
acggacatca cccggcgctg ttaatgtggc acatttcaaa cgaatacggg ggagattgcc    2400
actgtgattt atgccagcat gctttccggg agtggctgaa atcgaaatat gacaacagcc    2460
tcaagacatt gaaccatgcg tggtggaccc ctttttggag ccatacgttc aatgactggt    2520
cacaaattga aagcccttcg ccgatcggtg aaaatggctt gcatggcctg aatttagatt    2580
ggcgccggtt cgtcaccgat caaacgattt cgttttatga aaatgaaatc attccgctga    2640
aagaattgac gcctgatatc cctatcacaa cgaattttat ggctgacaca ccggatttga    2700
tcccgtatac cgttcgtata gcatacatta tacgaagtta tgccatagtg actggcgatg    2760
ctgtcggaat ggacgatcgg caatagttac ccttattatc aagataagaa agaaaaggat    2820
ttttcgctac gctcaaatcc tttaaaaaaa cacaaaagac cacatttttt aatgtggtct    2880
tttattcttc aactaaagca cccattagtt caacaaacga aaattggata agtgggata    2940 ttttttaaaat atatatttat gttacagtaa tattgacttt taaaaaagga ttgattctaa    3000
tgaagaaagc agacaagtaa gcctcctaaa ttcactttag ataaaaattt aggaggcata    3060
tcaaatgaac tttaataaaa ttgatttaga caattggaag agaaaagaga tatttaatca    3120
ttatttgaac caacaaacga cttttagtat aaccacagaa attgatatta gtgttttata    3180
ccgaaacata aaacaagaag gatataaatt ttaccctgca tttatttttct tagtgacaag    3240 ggtgataaac tcaaatacag cttttagaac tggttacaat agcgacgag agttaggtta    3300 ttgggataag ttagagccac tttatacaat ttttgatggt gtatctaaaa cattctctgg    3360
```

```
tatttggact cctgtaaaga atgacttcaa agagttttat gatttatacc tttctgatgt    3420
agagaaatat aatggttcgg ggaaattgtt cccaaaaca cctatacctg aaaatgcttt     3480
ttctctttct attattccat ggacttcatt tactgggttt aacttaaata tcaataataa   3540
tagtaattac cttctaccca ttattacagc aggaaaattc attaataaag gtaattcaat   3600
atatttaccg ctatctttac aggtacatca ttctgtttgt gatggttatc atgcaggatt   3660
gtttatgaac tctattcagg aattgtcaga taggcctaat gactggcttt tataatatga   3720
gataatgccg actgtacttt ttacagtcgg ttttctaaaa cgatacatta ataggtacga   3780
aaaagcaact tttttgcgc ttaaaaccag tcataccaat aaataacttc gtatagcata    3840
cattatacga acggtacgga attccgttaa ttcagaacgc tcggttgccg ccgggcgttt   3900
tttatgcagc aatggcaaga acgtcccggg gagctcctaa cttataggggg taacacttaa  3960 aaagaatca ataacgatag aaaccgctcc taaagcaggt gcattttttc ctaacgaaga    4020
aggcaatagt tcacatttat tgtctaaatg agaatggact ctagaagaaa cttcgttttt   4080
aatcgtattt aaaacaatgg gatgagattc aattatatga tttctcaaga taacagcttc   4140
tatatcaaat gtattaagga tattggttaa tccaattccg atataaaagc caaagttttg   4200
aagtgcattt aacatttcta catcattttt atttgcgcgt tccacaatct cttttcgaga   4260
atattctttt tcttctttag agagcgaagc cagtaacgct ttttcagaag catataattc   4320
ccaacagcct cgatttccac agctgcattt gggtccatta aaatctatcg tcatatgacc   4380
catttcccca gaaaaccct gaacaccttt atacaattcg ttgttaataa caagtccagt    4440
tccaattccg atattaatac tgatgtaaac gatgttttca tagttttttg tcataccaaa   4500 tacttttca ccgtatgctc ctgcattagc ttcattttca acaaaaaccg gaacattaaa    4560
ctcactctca attaaaaact gcaaatcttt gatattccaa tttaagttag gcatgaaaat   4620
aatttgctga tgacgatcta caaggcctgg aacacaaatt cctattccga ctagaccata   4680
aggggactca ggcatatggg ttacaaaacc atgaataagt gcaaataaaa tctcttttac   4740
ttcactagcg gaagaactag acaagtcaga agtcttctcg agaataatat ttccttctaa   4800
gtcggttaga attccgttaa gatagtcgac tcctatatca ataccaatcg agtagcctgc   4860
attcttatta aaaacaagca ttacaggtct tctgccgcct ctagattgcc ctgccccaat   4920
ttcaaaaata aaatcttttt caagcagtgt atttacttga gaggagacag tagacttgtt   4980
taatcctgta atctcagaga gagttgccct ggagacaggg gagttcttca aaatttcatc   5040
taatattaat ttttgattca tttttttac taaagcttga tctgcaattt gaataataac    5100
cactcctttg tttatccacc gaactaagtt ggtgtttttt gaagcttgaa ttagatattt   5160 aaagtatca tatctaatat tataactaaa ttttctaaaa aaacattga aataaacatt     5220 tatttgtat atgatgagat aaagttagtt tattggataa acaaactaac tcaattaaga    5280
tagttgatgg ataaacttgt tcacttaaat caaaggggga aatgacaaat ggtccaaact   5340
agtgatatct aaaaatcaaa gggggaaatg ggatccatgg ataagaaata ctcaataggc   5400
ttagctatcg gcacaaatag cgtcggatgg gcggtgatca ctgatgaata taaggttccg   5460
tctaaaaagt tcaaggttct gggaaataca gaccgccaca gtatcaaaaa aaatcttata   5520
ggggctcttt tatttgacag tggagagaca gcggaagcga ctcgtctcaa acggacagct   5580
cgtagaaggt atacacgtcg gaagaatcgt atttgttatc tacaggagat ttttcaaat    5640 gagatggcga agtagatga tagtttcttt catcgacttg aagagtcttt tttggtggaa    5700
```

```
gaagacaaga agcatgaacg tcatcctatt tttggaaata tagtagatga agttgcttat    5760
catgagaaat atccaactat ctatcatctg cgaaaaaaat tggtagattc tactgataaa    5820
gcggatttgc gcttaatcta tttggcctta gcgcatatga ttaagtttcg tggtcatttt    5880
ttgattgagg gagatttaaa tcctgataat agtgatgtgg acaaactatt tatccagttg    5940
gtacaaacct acaatcaatt atttgaagaa aaccctatta acgcaagtgg agtagatgct    6000
aaagcgattc tttctgcacg attgagtaaa tcaagacgat tagaaaatct cattgctcag    6060
ctccccggtg agaagaaaaa tggcttattt gggaatctca ttgctttgtc attgggtttg    6120
acccctaatt ttaaatcaaa ttttgatttg cagaagatg ctaaattaca gctttcaaaa     6180
gatacttacg atgatgattt agataattta ttggcgcaaa ttggagatca atatgctgat    6240 ttgttttttgg cagctaagaa tttatcagat gctattttac tttcagatat cctaagagta    6300
aatactgaaa taactaaggc tcccctatca gcttcaatga ttaaacgcta cgatgaacat    6360
catcaagact tgactctttt aaagctttta gttcgacaac aacttccaga aaagtataaa    6420
gaaatctttt ttgatcaatc aaaaaacgga tatgcaggtt atattgatgg gggagctagc    6480
caagaagaat tttataaatt tatcaaacca attttagaaa aaatggatgg tactgaggaa    6540
ttattggtga aactaaatcg tgaagatttg ctgcgcaagc aacggacctt tgacaacggc    6600
tctattcccc atcaaattca cttgggtgag ctgcatgcta ttttgagaag acaagaagac    6660
ttttatccat ttttaaaaga caatcgtgag aagattgaaa aaatcttgac ttttcgaatt    6720
ccttattatg ttggtccatt ggcgcgtggc aatagtcgtt ttgcatggat gactcggaag    6780
tctgaagaaa caattacccc atggaatttt gaagaagttg tcgataaagg tgcttcagct    6840
caatcattta ttgaacgcat gacaaacttt gataaaaatc ttccaaatga aaaagtacta    6900
ccaaaacata gtttgcttta tgagtatttt acggtttata acgaattgac aaaggtcaaa    6960
tatgttactg aaggaatgcg aaaaccagca tttctttcag gtgaacagaa gaaagccatt    7020
gttgatttac tcttcaaaac aaatcgaaaa gtaaccgtta agcaattaaa agaagattat    7080
ttcaaaaaaa tagaatgttt tgatagtgtt gaaatttcag gagttgaaga tagatttaat    7140
gcttcattag gtacctacca tgatttgcta aaaattatta aagataaaga ttttttggat    7200
aatgaagaaa atgaagatat cttagaggat attgttttaa cattgacctt atttgaagat    7260
agggagatga ttgaggaaag acttaaaaca tatgctcacc tctttgatga taaggtgatg    7320
aaacagctta aacgtcgccg ttatactggt tggggacgtt tgtctcgaaa attgattaat    7380
ggtattaggg ataagcaatc tggcaaaaca atattagatt ttttgaaatc agatggtttt    7440
gccaatcgca atttttatgca gctgatccat gatgatagtt tgacatttaa agaagacatt    7500
caaaaagcac aagtgtctgg acaaggcgat agtttacatg aacatattgc aaatttagct    7560
ggtagccctg ctattaaaaa aggtattttta cagactgtaa agttgttga tgaattggtc    7620 aaagtaatgg ggcggcataa gccagaaaat atcgttattg aaatggcacg tgaaaatcag    7680
acaactcaaa agggccagaa aaattcgcga gagcgtatga acgaatcga agaaggtatc    7740 aaagaattag gaagtcagat tcttaaagag catcctgttg aaaatactca attgcaaaat    7800
gaaaagctct atctctatta tctccaaaat ggaagagaca tgtatgtgga ccaagaatta    7860
gatattaatc gtttaagtga ttatgatgtc gatgccattg ttccacaaag tttccttaaa    7920
gacgattcaa tagacaataa ggtcttaacg cgttctgata aaaatcgtgg taaatcggat    7980
aacgttccaa gtgaagaagt agtcaaaaag atgaaaaact attggagaca acttctaaac    8040
gccaagttaa tcactcaacg taagtttgat aatttaacga aagctgaacg tggaggtttg    8100
```

```
agtgaacttg ataaagctgg ttttatcaaa cgccaattgg ttgaaactcg ccaaatcact   8160
aagcatgtgg cacaaatttt ggatagtcgc atgaatacta aatacgatga aaatgataaa   8220
cttattcgag aggttaaagt gattacctta aaatctaaat tagtttctga cttccgaaaa   8280
gatttccaat tctataaagt acgtgagatt aacaattacc atcatgccca tgatgcgtat   8340
ctaaatgccg tcgttggaac tgctttgatt aagaaatatc caaaacttga atcggagttt   8400
gtctatggtg attataaagt ttatgatgtt cgtaaaatga ttgctaagtc tgagcaagaa   8460
ataggcaaag caaccgcaaa atatttcttt tactctaata tcatgaactt cttcaaaaca   8520
gaaattacac ttgcaaatgg agagattcgc aaacgccctc taatcgaaac taatggggaa   8580
actggagaaa ttgtctggga taaagggcga gattttgcca cagtgcgcaa agtattgtcc   8640
atgccccaag tcaatattgt caagaaaaca gaagtacaga caggcggatt ctccaaggag   8700
tcaattttac caaaagaaa ttcggacaag cttattgctc gtaaaaaaga ctgggatcca   8760 aaaaatatg gtggttttga tagtccaacg gtagcttatt cagtcctagt ggttgctaag   8820
gtggaaaaag ggaaatcgaa gaagttaaaa tccgttaaag agttactagg gatcacaatt   8880
atggaaagaa gttcctttga aaaaaatccg attgactttt tagaagctaa aggatataag   8940
gaagttaaaa aagacttaat cattaaacta cctaaatata gtcttttttga gttagaaaac   9000 ggtcgtaaac ggatgctggc tagtgccgga gaattacaaa aaggaaatga gctggctctg   9060
ccaagcaaat atgtgaattt tttatattta gctagtcatt atgaaaagtt gaagggtagt   9120
ccagaagata cgaacaaaa acaattgttt gtggagcagc ataagcatta tttagatgag   9180
attattgagc aaatcagtga attttctaag cgtgttattt tagcagatgc caatttagat   9240
aaagttctta gtgcatataa caaacataga gacaaaccaa tacgtgaaca agcagaaaat   9300
attattcatt tatttacgtt gacgaatctt ggagctcccg ctgcttttaa atattttgat   9360
acaacaattg atcgtaaacg atatacgtct acaaaagaag ttttagatgc cactcttatc   9420
catcaatcca tcactggtct ttatgaaaca cgcattgatt tgagtcagct aggaggtgac   9480
taactcgagt aaggatctcc aggcatcaaa taaaacgaaa ggctcagtcg aaagactggg   9540
cctttcgttt tatctgttgt ttgtcggtga acgctctcta ctagagtcac actggctcac   9600
cttcgggtgg gcctttctgc gtttatacct agggatatat tccgcttcct cgctcactgc   9660
agcgtcatca cgaaagaaca agacttttca ccatataaac tgctgatcgt cccgatgctg   9720
tatttaatca gcgaggacac cgtttcccgt ttaaaagcgt ttacggctga cggcggcacc   9780
ttagtcatga cgtatatcag cggggttgtg aatgagcatg acttaacata cacaggcgga   9840
tggcatccgg atcttcaagc tatatttgga gttgagcctc ttgaaacgga caccctgtat   9900
ccgaaggatc gaaacgctgt cagctaccgc agccaaatat atgaaatgaa ggattatgca   9960
accgtgattg atgtaaagac agcttcagtg gaagcggtgt atcaagaaga ttttatgcg   10020 cgcacgccag cggtcacaag ccatgagtat cagcagggca aggcgtattt tatcggcgcg   10080
cgtttggagg atcaatttca gcgtgatttc tatgagggtc tgatcacaga cctgtctctc   10140
tctccagttt ttccggttcg gcacggaaaa ggcgtctccg tacaagcgag caggatcag   10200 gacaatgatt atatttttgt catgaatttc acggaagaaa aacagctggt cacgtttgat   10260
cagagtgtga aggacataat gacaggagac atattgtcag gcgacctgac gatggaaaag   10320
tatgaagtga gaattgtcgt aaacacacat taggggtac ccc                     10363

<210> SEQ ID NO 6
```

<211> LENGTH: 6179
<212> TYPE: DNA
<213> ORGANISM: Artificial Sequence
<220> FEATURE:
<223> OTHER INFORMATION: Synthetic DNA

<400> SEQUENCE: 6

| | | | | | |
|---|---|---|---|---|---|
| tcgagttcat | gtgcagctcc | atcagcaaaa | ggggatgata | agtttatcac | caccgactat | 60 |
| ttgcaacagt | gccgttgatc | gtgctatgat | cgactgatgt | catcagcggt | ggagtgcaat | 120 |
| gtcatgaggg | aagcggtgat | cgccgaagta | tcgactcaac | tatcagaggt | agttggcgtc | 180 |
| atcgagcgcc | atctcgaacc | gacgttgctg | gccgtacatt | tgtacggctc | cgcagtggat | 240 |
| ggcggcctga | agccacacag | tgatattgat | ttgctggtta | cggtgaccgt | aaggcttgat | 300 |
| gaaacaacgc | ggcgagcttt | gatcaacgac | cttttggaaa | cttcggcttc | ccctggagag | 360 |
| agcgagattc | tccgcgctgt | agaagtcacc | attgttgtgc | acgacgacat | cattccgtgg | 420 |
| cgttatccag | ctaagcgcga | actgcaattt | ggagaatggc | agcgcaatga | cattcttgca | 480 |
| ggtatcttcg | agccagccac | gatcgacatt | gatctgctta | tcttgctgac | aaaagcaaga | 540 |
| gaacatagcg | ttgccttggt | aggtccagcg | gcggaggaac | tctttgatcc | ggttcctgaa | 600 |
| caggatctat | ttgaggcgct | aaatgaaacc | ttaacgctat | ggaactcgcc | gcccgactgg | 660 |
| gctggcgatg | agcgaaatgt | agtgcttacg | ttgtcccgca | tttggtacag | cgcagtaacc | 720 |
| ggcaaaatcg | cgccgaagga | tgtcgctgcc | gactgggcaa | tggagcgcct | gccggcccag | 780 |
| tatcagcccg | tcatacttga | agctagacag | gcttatcttg | acaagaaga | agatcgcttg | 840 |
| gcctcgcgcg | cagatcagtt | ggaagaattt | gtccactacg | tgaaaggcga | gatcaccaag | 900 |
| gtagtcggca | aataagatgc | cgctcgccag | tcgattggct | gagctcatga | agttcctatt | 960 |
| ccgaagttcc | gcgaacgcgt | aaaggatcta | ggtgaagatc | cttttgata | atctcatgac | 1020 |
| caaaatccct | taacgtgagt | tttcgttcca | ctgagcgtca | gaccccgtag | aaaagatcaa | 1080 |
| aggatcttct | tgagatcctt | tttttctgcg | cgtaatctgc | tgcttgcaaa | caaaaaaacc | 1140 |
| accgctacca | gcggtggttt | gtttgccgga | tcaagagcta | ccaactcttt | ttccgaaggt | 1200 |
| aactggcttc | agcagagcgc | agataccaaa | tactgtcctt | ctagtgtagc | cgtagttagg | 1260 |
| ccaccacttc | aagaactctg | tagcaccgcc | tacatacctc | gctctgctaa | tcctgttacc | 1320 |
| agtggctgct | gccagtggcg | ataagtcgtg | tcttaccggg | ttggactcaa | gacgatagtt | 1380 |
| accggataag | gcgcagcggt | cgggctgaac | ggggggttcg | tgcacacagc | ccagcttgga | 1440 |
| gcgaacgacc | tacaccgaac | tgagatacct | acagcgtgag | ctatgagaaa | gcgccacgct | 1500 |
| tcccgaaggg | agaaaggcgg | acaggtatcc | ggtaagcggc | agggtcggaa | caggagagcg | 1560 |
| cacgagggag | cttccagggg | gaaacgcctg | gtatctttat | agtcctgtcg | ggtttcgcca | 1620 |
| cctctgactt | gagcgtcgat | ttttgtgatg | ctcgtcaggg | gggcggagcc | tatggaaaaa | 1680 |
| cgccagcaac | gcggcctttt | tacggttcct | ggccttttgc | tggccttttg | ctcacatgtt | 1740 |
| ctttcctgcg | ttatccctg | attctgtgga | taaccgtatt | accgcctttg | agtgagctga | 1800 |
| taccgctcgc | cgcagccgaa | cgaccgagcg | cagcgagtca | gtgagcgagg | aagcggaaga | 1860 |
| gcgcctgatg | cggtattttc | tccttacggg | aattccatat | ggattccgtg | atgtcaaagc | 1920 |
| ttgaaaaaac | gcacgtaaca | aaagcaaaat | ttatgctcca | tgggggagac | tacaaccccg | 1980 |
| atcagtggct | ggatcggccc | gatattttag | ctgacgatat | caaactgatg | aagctttctc | 2040 |
| atacgaatac | gttttctgtc | ggcatttttg | catggagcgc | acttgagccg | gaggagggcg | 2100 |
| tatatcaatt | tgaatggctg | gatgatattt | ttgagcggat | tcacagtata | ggcggccggg | 2160 |

```
tcatattagc aacgccgagc ggagcccgtc cggcctggct gtcgcaaacc tatccggaag    2220
ttttgcgcgt caatgcctcc cgcgtcaaac agctgcacgg cggaaggcac aaccactgcc    2280
tcacatctaa agtctaccga gaaaaaacac ggcacatcaa ccgcttatta gcagaacgat    2340
acggacatca cccggcgctg ttaatgtggc acatttcaaa cgaatacggg ggagattgcc    2400
actgtgattt atgccagcat gctttccggg agtggctgaa atcgaaatat gacaacagcc    2460
tcaagacatt gaaccatgcg tggtggaccc cttttggag ccatacgttc aatgactggt     2520
cacaaattga aagcccttcg ccgatcggtg aaaatggctt gcatggcctg aatttagatt    2580
ggcgccggtt cgtcaccgat caaacgattt cgttttatga aaatgaaatc attccgctga    2640
aagaattgac gcctgatatc cctatcacaa cgaattttat ggctgacaca ccggatttga    2700
tcccgtatac cgttcgtata gcatacatta tacgaagtta tgccatagtg actggcgatg    2760
ctgtcggaat ggacgacggc aatagttacc cttattatca agataagaaa gaaaaggatt    2820
tttcgctacg ctcaaatcct ttaaaaaaac acaaaagacc acattttta atgtggtctt      2880 ttattcttca actaaagcac ccattagttc aacaaacgaa aattggataa agtgggatat    2940
ttttaaaata tatatttatg ttacagtaat attgactttt aaaaaaggat tgattctaat    3000
gaagaaagca gacaagtaag cctcctaaat tcactttaga taaaaattta ggaggcatat    3060
caaatgaact ttaataaaat tgatttagac aattggaaga gaaagagat atttaatcat      3120 tatttgaacc aacaaacgac ttttagtata accacagaaa ttgatattag tgttttatac    3180
cgaaacataa aacaagaagg atataaattt taccctgcat ttattttctt agtgacaagg    3240
gtgataaact caaatacagc ttttagaact ggttacaata gcgacggaga gttaggttat    3300
tgggataagt tagagccact ttatacaatt tttgatggtg tatctaaaac attctctggt    3360
atttggactc ctgtaaagaa tgacttcaaa gagttttatg atttatacct ttctgatgta    3420
gagaaatata atggttcggg gaaattgttt cccaaaacac ctatacctga aaatgctttt    3480
tctctttcta ttattccatg gacttcattt actgggttta acttaaatat caataataat    3540
agtaattacc ttctacccat tattacagca ggaaaattca ttaataaagg taattcaata    3600
tatttaccgc tatctttaca ggtacatcat tctgtttgtg atggttatca tgcaggattg    3660
tttatgaact ctattcagga attgtcagat aggcctaatg actggctttt ataatatgag    3720
ataatgccga ctgtacttt tacagtcggt tttctaacga tacattaata ggtacgaaaa     3780
agcaactttt tttgcgctta aaaccagtca taccaataaa taacttcgta tagcatacat    3840
tatacgaacg gtattcagaa cgctcggttg ccgccgggcg ttttttatgc agcaatggca    3900
agaacgtccc ggggagctcc taacttatag gggtaacact taaaaagaa tcaataacga     3960 tagaaaccgc tcctaaagca ggtgcatttt ttcctaacga agaaggcaat agttcacatt    4020
tattgtctaa atgagaatgg actctagaag aaacttcgtt tttaatcgta tttaaaacaa    4080
tgggatgaga ttcaattata tgattctca agataacagc ttctatatca aatgtattaa     4140
ggatattggt taatccaatt ccgatataaa agccaaagtt ttgaagtgca tttaacattt    4200
ctacatcatt tttatttgcg cgttccacaa tctcttttcg agaaatattc ttttcttctt    4260
tagagagcga agccagtaac gcttttttcag aagcatataa ttcccaacag cctcgatttc    4320
cacagctgca tttgggtcca ttaaaatcta tcgtcatatg acccatttcc ccagaaaaac    4380
cctgaacacc tttatacaat tcgttgttaa taacaagtcc agttccaatt ccgatattaa    4440
tactgatgta aacgatgttt tcatagtttt ttgtcatacc aaatacttt tcaccgtatg      4500
```

-continued

```
ctcctgcatt agcttcattt tcaacaaaaa ccggaacatt aaactcactc tcaattaaaa    4560
actgcaaatc tttgatattc caatttaagt taggcatgaa ataaatttgc tgatgacgat    4620
ctacaaggcc tggaacacaa attcctattc cgactagacc ataaggggac tcaggcatat    4680
gggttacaaa accatgaata agtgcaaata aaatctcttt tacttcacta gcggaagaac    4740
tagacaagtc agaagtcttc tcgagaataa tatttccttc taagtcggtt agaattccgt    4800
taagatagtc gactcctata tcaataccaa tcgagtagcc tgcattctta ttaaaaacaa    4860
gcattacagg tcttctgccg cctctagatt gccctgcccc aatttcaaaa ataaaatctt    4920
tttcaagcag tgtatttact tgagaggaga cagtagactt gtttaatcct gtaatctcag    4980
agagagttgc cctggagaca ggggagttct tcaaaatttc atctaatatt aatttttgat    5040
tcatttttt tactaaagct tgatctgcaa tttgaataat aaccactcct ttgtttatcc    5100
accgaactaa gttggtgttt tttgaagctt gaattagata tttaaaagta tcatatctaa    5160
tattataact aaattttcta aaaaaaacat tgaaataaac atttattttg tatatgatga    5220
gataaagtta gtttattgga taaacaaact aactcaatta agatagttga tggataaact    5280
tgttcactta aatcaaaggg ggaaatgaca aatggtccaa actagtgata tctaaaaatc    5340
aaaggggaa atgggatcca ttaccctgtc tgcaggggcg ctcgaggatg ctcagggtt    5400
tgcgaaggcg acaaaacgtt atccgcaaac gcttcagcag cattaccgca cattctggga    5460
acacgatatc cctgtcgacg tcatcacgaa agaacaagac ttttcaccat ataaactgct    5520
gatcgtcccg atgctgtatt taatcagcga ggacaccgtt tcccgtttaa aagcgtttac    5580
ggctgacggc ggcaccttag tcatgacgta tatcagcggg gttgtgaatg agcatgactt    5640
aacatacaca ggcggatggc atccggatct tcaagctata tttggagttg agcctcttga    5700
aacgacacc ctgtatccga aggatcgaaa cgctgtcagc taccgcagcc aaatatatga    5760
aatgaaggat tatgcaaccg tgattgatgt aaagacagct tcagtggaag cggtgtatca    5820
agaagatttt tatgcgcgca cgccagcggt cacaagccat gagtatcagc agggcaaggc    5880
gtattttatc ggcgcgcgtt tggaggatca atttcagcgt gatttctatg agggtctgat    5940
cacagacctg tctctctctc cagtttttcc ggttcggcac ggaaaaggcg tctccgtaca    6000
agcgaggcag gatcaggaca atgattatat ttttgtcatg aatttcacgg aagaaaaaca    6060
gctggtcacg tttgatcaga gtgtgaagga cataatgaca ggagacatat tgtcaggcga    6120
cctgacgatg gaaaagtatg aagtgagaat tgtcgtaaac acacattagg gggtacccc    6179
```

<210> SEQ ID NO 7
<211> LENGTH: 4642
<212> TYPE: DNA
<213> ORGANISM: Artificial Sequence
<220> FEATURE:
<223> OTHER INFORMATION: Synthetic DNA

<400> SEQUENCE: 7

```
cagctccatc agcaaaaggg gatgataagt ttatcaccac cgactatttg caacagtgcc      60
gttgatcgtg ctatgatcga ctgatgtcat cagcggtgga gtgcaatgtc atgagggaag     120
cggtgatcgc cgaagtatcg actcaactat cagaggtagt tggcgtcatc gagcgccatc     180
tcgaaccgac gttgctggcc gtacatttgt acggctccgc agtggatggc ggcctgaagc     240
cacacagtga tatttgatttg ctggttacgg tgaccgtaag gcttgatgaa acaacgcggc     300
gagctttgat caacgacctt ttggaaactt cggcttcccc tggagagagc gagattctcc     360
gcgctgtaga agtcaccatt gttgtgcacg acgacatcat tccgtggcgt tatccagcta     420
```

```
agcgcgaact gcaatttgga gaatggcagc gcaatgacat tcttgcaggt atcttcgagc    480
cagccacgat cgacattgat ctggctatct tgctgacaaa agcaagagaa catagcgttg    540
ccttggtagg tccagcggcg gaggaactct ttgatccggt tcctgaacag gatctatttg    600
aggcgctaaa tgaaaccttg acgctatgga actcgccgcc cgactgggct ggcgatgagc    660
gaaatgtagt gcttacgttg tcccgcattt ggtacagcgc agtaaccggc aaaatcgcgc    720
cgaaggatgt cgctgccgac tgggcaatgg agcgcctgcc ggcccagtat cagcccgtca    780
tacttgaagc tagacaggct tatcttggac aagaagaaga tcgcttggcc tcgcgcgcag    840
atcagttgga gaatttgtc cactacgtga aaggcgagat caccaaggta gtcggcaaat    900
aagatgccgc tcgccagtcg attggctgag ctcatgaagt tcctattccg aagttccgcg    960
aacgcgtaaa ggatctaggt gaagatcctt tttgataatc tcatgaccaa aatcccttaa    1020
cgtgagtttt cgttccactg agcgtcagac cccgtagaaa agatcaaagg atcttcttga    1080 gatcctttt ttctgcgcgt aatctgctgc ttgcaaacaa aaaaaccacc gctaccagcg    1140
gtggtttgtt tgccggatca agagctacca actctttttc cgaaggtaac tggcttcagc    1200
agagcgcaga taccaaatac tgtccttcta gtgtagccgt agttaggcca ccacttcaag    1260
aactctgtag caccgcctac atacctcgct ctgctaatcc tgttaccagt ggctgctgcc    1320
agtggcgata gtcgtgtct taccggggttg gactcaagac gatagttacc ggataaggcg    1380
cagcggtcgg gctgaacggg gggttcgtgc acacagccca gcttggagcg aacgacctac    1440
accgaactga gatacctaca gcgtgagcta tgagaaagcg ccacgcttcc cgaagggaga    1500
aaggcggaca ggtatccggt aagcggcagg gtcggaacag gagagcgcac gagggagctt    1560 ccaggggaa acgcctggta tctttatagt cctgtcgggt ttcgccacct ctgacttgag    1620
cgtcgatttt tgtgatgctc gtcagggggg cggagcctat ggaaaaacgc cagcaacgcg    1680
gcctttttac ggttcctggc cttttgctgg ccttttgctc acatgttctt tcctgcgtta    1740 tccctgatt ctgtggataa ccgtattacc gcctttgagt gagctgatac cgctcgccgc    1800
agccgaacga ccgagcgcag cgagtcagtg agcgaggaag cggaagagcg cctgatgcgg    1860
tatttttctc cttacgcatct gtgcggtatt tcacaccgca tatgctggat ccgcgatgtt    1920
tgcaaaacga ttcaaaacct cttactgcc gttattcgct ggattttat tgctgtttca    1980 tttggttctg gcaggaccgg cggctgcgag tgctgaaacg gcgaacaaat cgaatgagct    2040
tacagcaccg tcgatcaaaa gcggaaccat tcttcatgca tggaattggt cgttcaatac    2100
gttaaaacac aatatgaagg atattcatga tgcaggatat acagccattc agacatctcc    2160
gattaaccaa gtaaaggaag ggaatcaagg agataaaagc atgtcgaact ggtactggct    2220
gtatcagccg acatcgtatc aaattggcaa ccgttactta ggtactgaac aagaatttaa    2280
agaaatgtgt gcagccgctg aagaatatgg cataaaggtc attgttgacg cggtcatcaa    2340
tcataccacc agtgattatg ccgcgatttc caatgaggtt aagagtattc caaactggac    2400
acatggaaac acacaaatta aaaactggtc tgatcgatgg gatgtcacgc agaacatgcc    2460
atggcatgag attctaccgt tcgtatagca tacattatac gaagttatct tgatatggct    2520
ttttatatgt gttactctac atacagaaag gaggaactaa atatggccaa gttgaccagt    2580
gccgttccgg tgctcaccgc gcgcgacgtc gccggagcgg tcgagttctg gaccgaccgg    2640
ctcgggttct cccgggactt cgtggaggac gacttcgccg tgtgtggccgg ggacgacgtg    2700 accctgttca tcagcgcggt ccaggaccag gtggtgccgg acaacaccct ggcctgggtg    2760
```

```
tgggtgcgcg gcctggacga gctgtacgcc gagtggtcgg aggtcgtgtc cacgaacttc    2820
cgggacgcct ccgggccggc catgaccgag atcggcgagc agccgtgggg gcgggagttc    2880
gccctgcgcg acccggccgg caactgcgtg cacttcgtgg ccgaggagca ggactgaata    2940
acttcgtata gcatacatta tacgaacggt aaatcgtcga caggtcgtcg acctgcaggc    3000
ttattaacgt tgatataatt taaattttat ttgacaaaaa tgggctcgtg ttgtacaata    3060
aatgtcgaag atcctcatta gaccagtttt agagctagaa atagcaagtt aaaataaggc    3120
tagtccgtta tcaacttgaa aaagtggcac cgagtcggtg cttttttttga attccgccac    3180 cgtcgacctg caggcttatt aacgttgata taatttaaat tttatttgac aaaaatgggc    3240
tcgtgttgta caataaatgt ccgattgtaa atcagtgcc gttttagagc tagaaatagc     3300
aagttaaaat aaggctagtc cgttatcaac ttgaaaaagt ggcaccgagt cggtgctttt    3360
tttgaattcc ggtacgtcga cctgcaggct tattaacgtt gatataattt aaattttatt    3420
tgacaaaaat gggctcgtgt tgtacaataa atgttatcct caggttcgtc catcgtttta    3480
gagctagaaa tagcaagtta aaataaggct agtccgttat caacttgaaa aagtggcacc    3540
gagtcggtgc ttttttttgaa ttccgccgat cgacatggat gagcgatgat gatatccgtt    3600
taggctgggc ggtgatagct tctcgttcag gcagtacgcc tcttttcttt tccagacctg    3660
agggaggcgg aaatggtgtg aggttcccgg ggaaaagcca aataggcgat cgcgggagtg    3720
ctttatttga agatcaggct atcactgcgg tcaatagatt tcacaatgtg atggctggac    3780
agcctgagga actctcgaac ccgaatggaa acaaccagat atttatgaat cagcgcggct    3840 cacatgcgt tgtgctggca aatgcaggtt catcctctgt ctctatcaat acggcaacaa    3900
aattgcctga tggcaggtat gacaataaag ctggagcggg ttcatttcaa gtgaacgatg    3960
gtaaactgac aggcacgatc aatgccaggt ctgtagctgt gctttatcct gatgatattg    4020
caaaagcgcc tcatgttttc cttgagaatt acaaaacagg tgtaacacat tctttcaatg    4080
atcaactgac gattaccttg cgtgcagatg cgaatacaac aaaagccgtt tatcaaatca    4140
ataatggacc agagacggcg tttaaggatg gagatcaatt cacaatcgga aaaggagatc    4200
catttggcaa acatacacc atcatgttaa aggaacgaa cagtgatggt gtaacgagga      4260
ccgagaaata cagttttgtt aaaagagatc cagcgtcggc caaaaccatc ggctatcaaa    4320
atccgaatca ttggagccag gtaaatgctt atatctataa acatgatggg agccgagtaa    4380
ttgaattgac cggatcttgg cctggaaaac caatgactaa aaatgcagac ggaatttaca    4440
cgctgacgct gcctgcggac acggatacaa ccaacgcaaa agtgattttt aataatggca    4500
gcgcccaagt gcccggtcag aatcagcctg gctttgatta cgtgctaaat ggtttatata    4560
atgactcggg cttaagcggt tctcttcccc attgacccaa gcttagatct attaccctgt    4620
tatccctact cgagttcatg tg                                             4642
```

<210> SEQ ID NO 8
<211> LENGTH: 4244
<212> TYPE: DNA
<213> ORGANISM: Artificial Sequence
<220> FEATURE:
<223> OTHER INFORMATION: Synthetic DNA

<400> SEQUENCE: 8

```
tcgagttcat gtgcagctcc atcagcaaaa ggggatgata agtttatcac caccgactat      60
ttgcaacagt gccgttgatc gtgctatgat cgactgatgt catcagcggt ggagtgcaat     120
gtcatgaggg aagcggtgat cgccgaagta tcgactcaac tatcagaggt agttggcgtc     180
```

```
atcgagcgcc atctcgaacc gacgttgctg gccgtacatt tgtacggctc cgcagtggat      240
ggcggcctga agccacacag tgatattgat ttgctggtta cggtgaccgt aaggcttgat      300
gaaacaacgc ggcgagcttt gatcaacgac cttttggaaa cttcggcttc ccctggagag      360
agcgagattc tccgcgctgt agaagtcacc attgttgtgc acgacgacat cattccgtgg      420
cgttatccag ctaagcgcga actgcaattt ggagaatggc agcgcaatga cattcttgca      480
ggtatcttcg agccagccac gatcgacatt gatctggcta tcttgctgac aaaagcaaga      540
gaacatagcg ttgccttggt aggtccagcg gcggaggaac tctttgatcc ggttcctgaa      600
caggatctat ttgaggcgct aaatgaaacc ttaacgctat ggaactcgcc gcccgactgg      660
gctggcgatg agcgaaatgt agtgcttacg ttgtcccgca tttggtacag cgcagtaacc      720
ggcaaaatcg cgccgaagga tgtcgctgcc gactgggcaa tggagcgcct gccggcccag      780
tatcagcccg tcatacttga agctagacag gcttatcttg acaagaaga agatcgcttg       840 gcctcgcgcg cagatcagtt ggaagaattt gtccactacg tgaaaggcga gatcaccaag      900
gtagtcggca aataagatgc cgctcgccag tcgattggct gagctcatga agttcctatt      960
ccgaagttcc gcgaacgcgt aaaggatcta ggtgaagatc cttttttgata atctcatgac    1020 caaaatccct taacgtgagt tttcgttcca ctgagcgtca gaccccgtag aaaagatcaa    1080
aggatcttct tgagatcctt tttttctgcg cgtaatctgc tgcttgcaaa caaaaaaacc    1140
accgctacca gcggtggttt gtttgccgga tcaagagcta ccaactcttt ttccgaaggt    1200
aactggcttc agcagagcgc agataccaaa tactgtcctt ctagtgtagc cgtagttagg    1260
ccaccacttc aagaactctg tagcaccgcc tacatacctc gctctgctaa tcctgttacc    1320
agtggctgct gccagtggcg ataagtcgtg tcttaccggg ttggactcaa gacgatagtt    1380
accggataag cgcagcggt cgggctgaac ggggggttcg tgcacacagc ccagcttgga    1440
gcgaacgacc tacaccgaac tgagatacct acagcgtgag ctatgagaaa gcgccacgct    1500
tcccgaaggg agaaaggcgg acaggtatcc ggtaagcggc agggtcggaa caggagagcg    1560
cacgagggag cttccagggg gaaacgcctg gtatctttat agtcctgtcg ggtttcgcca    1620
cctctgactt gagcgtcgat ttttgtgatg ctcgtcaggg gggcggagcc tatggaaaaa    1680
cgccagcaac gcggcctttt tacggttcct ggccttttgc tggccttttg ctcacatgtt    1740
ctttcctgcg ttatccctg attctgtgga taaccgtatt accgcctttg agtgagctga    1800
taccgctcgc cgcagccgaa cgaccgagcg cagcgagtca gtgagcgagg aagcggaaga    1860
gcgcctgatg cggtattttc tccttacgca tctgtgcggt atttcacacc gcatatgctg    1920
gatccgcgat gtttgcaaaa cgattcaaaa cctctttact gccgttattc gctggatttt    1980
tattgctgtt tcatttggtt ctggcaggac cggcggctgc gagtgctgaa acggcgaaca    2040
aatcgaatga gcttacagca ccgtcgatca aaagcggaac cattcttcat gcatggaatt    2100
ggtcgttcaa tacgttaaaa cacaatatga aggatattca tgatgcagga tatacagcca    2160
ttcagacatc tccgattaac caagtaaagg aagggaatca aggagataaa agcatgtcga    2220
actggtactg gctgtatcag ccgacatcgt atcaaattgg caaccgttac ttaggtactg    2280
aacaagaatt taaagaaatg tgtgcagccg ctgaagaata tggcataaag gtcattgttg    2340
acgcggtcat caatcatacc accagtgatt atgccgcgat ttccaatgag gttaagagta    2400
ttccaaactg gacacatgga aacacacaaa ttaaaaactg gtctgatcga tgggatgtca    2460
cgcagaacat gccatggcat gagattctac cgttcgtata gcatacatta tacgaagtta    2520
```

-continued

| | |
|---|---|
| tcttgatatg gcttttttata tgtgttactc tacatacaga aaggaggaac taaatatggc | 2580 |
| caagttgacc agtgccgttc cggtgctcac cgcgcgcgac gtcgccggag cggtcgagtt | 2640 |
| ctggaccgac cggctcgggt tctcccggga cttcgtggag gacgacttcg ccggtgtggt | 2700 |
| ccgggacgac gtgaccctgt tcatcagcgc ggtccaggac caggtggtgc cggacaacac | 2760 |
| cctggcctgg gtgtgggtgc gcggcctgga cgagctgtac gccgagtggt cggaggtcgt | 2820 |
| gtccacgaac ttccgggacg cctccgggcc ggccatgacc gagatcggcg agcagccgtg | 2880 |
| ggggcgggag ttcgccctgc gcgacccggc cggcaactgc gtgcacttcg tggccgagga | 2940 |
| gcaggactga ataacttcgt atagcataca ttatacgaac ggtaaatcgt cgacctgcag | 3000 |
| gcttattaac gttgatataa tttaaatttt atttgacaaa aatgggctcg tgttgtacaa | 3060 |
| taaatgtact agtcctcaaa ctggcagatg cacgttttag agctagaaat agcaagttaa | 3120 |
| aataaggcta gtccgttatc aacttgaaaa agtggcaccg agtcggtgct ttttttgaat | 3180 |
| tccgtcgaca tggatgagcg atgatgatat ccgtttaggc tgggcggtga tagcttctcg | 3240 |
| ttcaggcagt acgcctcttt tcttttccag acctgaggga ggcggaaatg gtgtgaggtt | 3300 |
| cccggggaaa agccaaatag gcgatcgcgg gagtgctttta tttgaagatc aggctatcac | 3360 |
| tgcggtcaat agatttcaca atgtgatggc tggacagcct gaggaactct cgaacccgaa | 3420 |
| tggaaacaac cagatattta tgaatcagcg cggctcacat ggcgttgtgc tggcaaatgc | 3480 |
| aggttcatcc tctgtctcta tcaatacggc aacaaaattg cctgatgca ggtatgacaa | 3540 |
| taaagctgga gcgggttcat ttcaagtgaa cgatggtaaa ctgacaggca cgatcaatgc | 3600 |
| caggtctgta gctgtgcttt atcctgatga tattgcaaaa gcgcctcatg ttttccttga | 3660 |
| gaattacaaa acaggtgtaa cacattcttt caatgatcaa ctgacgatta ccttgcgtgc | 3720 |
| agatgcgaat acaacaaaag ccgtttatca aatcaataat ggaccagaga cggcgtttaa | 3780 |
| ggatggagat caattcacaa tcggaaaagg agatccattt ggcaaaacat acaccatcat | 3840 |
| gttaaaagga acgaacagtg atggtgtaac gaggaccgag aaatacagtt ttgttaaaag | 3900 |
| agatccagcg tcggccaaaa ccatcggcta tcaaaatccg aatcattgga gccaggtaaa | 3960 |
| tgcttatatc tataaacatg atgggagccg agtaattgaa ttgaccggat cttggcctgg | 4020 |
| aaaaccaatg actaaaaatg cagacggaat ttacacgctg acgctgcctg cggacacgga | 4080 |
| tacaaccaac gcaaaagtga ttttaataa tggcagcgcc caagtgcccg gtcagaatca | 4140 |
| gcctggcttt gattacgtgc taaatggttt atataatgac tcgggcttaa gcggttctct | 4200 |
| tccccattga cccaagctta gatctattac cctgttatcc ctac | 4244 |

<210> SEQ ID NO 9
<211> LENGTH: 1928
<212> TYPE: DNA
<213> ORGANISM: Artificial Sequence
<220> FEATURE:
<223> OTHER INFORMATION: Synthetic DNA

<400> SEQUENCE: 9

| | |
|---|---|
| cacacattag ggggtacccc tcgagttcat gtgcagctcc atcagcaaaa ggggatgata | 60 |
| agtttatcac caccgactat ttgcaacagt gccgttgatc gtgctatgat cgactgatgt | 120 |
| catcagcggt ggagtgcaat gtcatgaggg aagcggtgat cgccgaagta tcgactcaac | 180 |
| tatcagaggt agttggcgtc atcgagcgcc atctcgaacc gacgttgctg gccgtacatt | 240 |
| tgtacggctc cgcagtggat ggcggcctga agccacacag tgatattgat ttgctggtta | 300 |
| cggtgaccgt aaggcttgat gaaacaacgc ggcgagcttt gatcaacgac cttttggaaa | 360 |

```
cttcggcttc ccctggagag agcgagattc tccgcgctgt agaagtcacc attgttgtgc      420
acgacgacat cattccgtgg cgttatccag ctaagcgcga actgcaattt ggagaatggc      480
agcgcaatga cattcttgca ggtatcttcg agccagccac gatcgacatt gatctggcta      540
tcttgctgac aaaagcaaga gaacatagcg ttgccttggt aggtccagcg gcggaggaac      600
tctttgatcc ggttcctgaa caggatctat ttgaggcgct aaatgaaacc ttaacgctat      660
ggaactcgcc gcccgactgg gctggcgatg agcgaaatgt agtgcttacg ttgtcccgca      720
tttggtacag cgcagtaacc ggcaaaatcg cgccgaagga tgtcgctgcc gactgggcaa      780
tggagcgcct gccggcccag tatcagcccg tcatacttga agctagacag gcttatcttg      840
gacaagaaga agatcgcttg gcctcgcgcg cagatcagtt ggaagaattt gtccactacg      900
tgaaaggcga gatcaccaag gtagtcggca aataagatgc cgctcgccag tcgattggct      960
gagctcatga agttcctatt ccgaagttcc gcgaacgcgt aaaggatcta ggtgaagatc     1020 cttttgata tctcatgac caaaatccct taacgtgagt tttcgttcca ctgagcgtca     1080
gaccccgtag aaaagatcaa aggatcttct tgagatcctt ttttttctgcg cgtaatctgc     1140 tgcttgcaaa caaaaaaacc accgctacca gcggtggttt gtttgccgga tcaagagcta     1200
ccaactcttt ttccgaaggt aactggcttc agcagagcgc agataccaaa tactgtcctt     1260
ctagtgtagc cgtagttagg ccaccacttc aagaactctg tagcaccgcc tacatacctc     1320
gctctgctaa tcctgttacc agtggctgct gccagtggcg ataagtcgtg tcttaccggg     1380
ttggactcaa gacgatagtt accggataag gcgcagcggt cgggctgaac ggggggttcg     1440
tgcacacagc ccagcttgga gcgaacgacc tacaccgaac tgagatacct acagcgtgag     1500
ctatgagaaa gcgccacgct tcccgaaggg agaaaggcgg acaggtatcc ggtaagcggc     1560
agggtcggaa caggagagcg cacgagggag cttccagggg gaaacgcctg gtatctttat     1620
agtcctgtcg ggtttcgcca cctctgactt gagcgtcgat ttttgtgatg ctcgtcaggg     1680
gggcggagcc tatggaaaaa cgccagcaac gcggccttt tacggttcct ggccttttgc     1740
tggccttttg ctcacatgtt ctttcctgcg ttatccctg attctgtgga taaccgtatt     1800
accgcctttg agtgagctga taccgctcgc cgcagccgaa cgaccgagcg cagcgagtca     1860
gtgagcgagg aagcggaaga gcgcctgatg cggtattttc tccttacggg aattccatat     1920
ggattccg                                                              1928
```

<210> SEQ ID NO 10
<211> LENGTH: 839
<212> TYPE: DNA
<213> ORGANISM: Artificial Sequence
<220> FEATURE:
<223> OTHER INFORMATION: Synthetic DNA

<400> SEQUENCE: 10

```
ggaattccat atggattccg tgatgtcaaa gcttgaaaaa acgcacgtaa caaaagcaaa       60
atttatgctc catgggggag actacaaccc cgatcagtgg ctggatcggc ccgatatttt      120
agctgacgat atcaaactga tgaagctttc tcatacgaat acgttttctg tcggcatttt      180
tgcatggagc gcacttgagc cggaggaggg cgtatatcaa tttgaatggc tggatgatat      240
ttttgagcgg attcacagta taggcggccg ggtcatatta gcaacgccga gcggagcccg      300
tccggcctgg ctgtcgcaaa cctatccgga agttttgcgc gtcaatgcct cccgcgtcaa      360
acagctgcac ggcggaaggc acaaccactg cctcacatct aaagtctacc gagaaaaaac      420
```

| | |
|---|---|
| acggcacatc aaccgcttat tagcagaacg atacggacat cacccggcgc tgttaatgtg | 480 |
| gcacatttca aacgaatacg ggggagattg ccactgtgat ttatgccagc atgctttccg | 540 |
| ggagtggctg aaatcgaaat atgacaacag cctcaagaca ttgaaccatg cgtggtggac | 600 |
| ccctttttgg agccatacgt tcaatgactg gtcacaaatt gaaagccctt cgccgatcgg | 660 |
| tgaaaatggc ttgcatggcc tgaatttaga ttggcgccgg ttcgtcaccg atcaaacgat | 720 |
| ttcgttttat gaaaatgaaa tcattccgct gaaagaattg acgcctgata tccctatcac | 780 |
| aacgaattt atggctgaca caccggattt gatcccgtat accgttcgta tagcataca | 839 |

<210> SEQ ID NO 11
<211> LENGTH: 1166
<212> TYPE: DNA
<213> ORGANISM: Artificial Sequence
<220> FEATURE:
<223> OTHER INFORMATION: Synthetic DNA

<400> SEQUENCE: 11

| | |
|---|---|
| taccgttcgt atagcataca ttatacgaag ttatgccata gtgactggcg atgctgtcgg | 60 |
| aatggacgac ggcaatagtt acccttatta tcaagataag aaagaaaagg attttttcgct | 120 |
| acgctcaaat cctttaaaaa aacacaaaag accacatttt ttaatgtggt cttttattct | 180 |
| tcaactaaag cacccattag ttcaacaaac gaaaattgga taaagtggga tattttaaa | 240 |
| atatatattt atgttacagt aatattgact tttaaaaaag gattgattct aatgaagaaa | 300 |
| gcagacaagt aagcctccta aattcacttt agataaaaat ttaggaggca tatcaaatga | 360 |
| actttaataa aattgattta gacaattgga agagaaaaga gatatttaat cattatttga | 420 |
| accaacaaac gacttttagt ataaccacag aaattgatat tagtgtttta taccgaaaca | 480 |
| taaaacaaga aggatataaa ttttaccctg catttatttt cttagtgaca agggtgataa | 540 |
| actcaaatac agcttttaga actggttaca atagcgacgg agagttaggt tattgggata | 600 |
| agttagagcc actttataca attttgatg gtgtatctaa aacattctct ggtatttgga | 660 |
| ctcctgtaaa gaatgacttc aaagagtttt atgatttata cctttctgat gtagagaaat | 720 |
| ataatggttc ggggaaattg tttcccaaaa cacctatacc tgaaaatgct ttttctcttt | 780 |
| ctattattcc atggacttca tttactgggt ttaacttaaa tatcaataat aatagtaatt | 840 |
| accttctacc cattattaca gcaggaaaat tcattaataa aggtaattca atatatttac | 900 |
| cgctatcttt acaggtacat cattctgttt gtgatggtta tcatgcagga ttgttttatga | 960 |
| actctattca ggaattgtca gataggccta atgactggct tttataatat gagataatgc | 1020 |
| cgactgtact ttttacagtc ggttttctaa cgatacatta ataggtacga aaaagcaact | 1080 |
| tttttttgcgc ttaaaaccag tcataccaat aaataacttc gtatagcata cattatacga | 1140 |
| acggtattca gaacgctcgg ttgccg | 1166 |

<210> SEQ ID NO 12
<211> LENGTH: 1500
<212> TYPE: DNA
<213> ORGANISM: Artificial Sequence
<220> FEATURE:
<223> OTHER INFORMATION: Synthetic DNA

<400> SEQUENCE: 12

| | |
|---|---|
| ttcagaacgc tcggttgccg ccgggcgttt tttatgcagc aatggcaaga acgtcccggg | 60 |
| gagctcctaa cttatagggg taacacttaa aaagaatca ataacgatag aaaccgctcc | 120 |
| taaagcaggt gcattttttc ctaacgaaga aggcaatagt tcacatttat tgtctaaatg | 180 |

| | |
|---|---|
| agaatggact ctagaagaaa cttcgttttt aatcgtattt aaaacaatgg gatgagattc | 240 |
| aattatatga tttctcaaga taacagcttc tatatcaaat gtattaagga tattggttaa | 300 |
| tccaattccg atataaaagc caaagttttg aagtgcattt aacatttcta catcattttt | 360 |
| atttgcgcgt tccacaatct cttttcgaga aatattcttt tcttctttag agagcgaagc | 420 |
| cagtaacgct ttttcagaag catataattc ccaacagcct cgatttccac agctgcattt | 480 |
| gggtccatta aaatctatcg tcatatgacc catttcccca gaaaaccct gaacacctt | 540 |
| atacaattcg ttgttaataa caagtccagt tccaattccg atattaatac tgatgtaaac | 600 |
| gatgttttca tagttttttg tcataccaaa tactttttca ccgtatgctc ctgcattagc | 660 |
| ttcattttca acaaaaaccg gaacattaaa ctcactctca attaaaaact gcaaatcttt | 720 |
| gatattccaa tttaagttag gcatgaaaat aatttgctga tgacgatcta caaggcctgg | 780 |
| aacacaaatt cctattccga ctagaccata aggggactca ggcatatggg ttacaaaacc | 840 |
| atgaataagt gcaaataaaa tctcttttac ttcactagcg gaagaactag acaagtcaga | 900 |
| agtcttctcg agaataatat ttccttctaa gtcggttaga attccgttaa gatagtcgac | 960 |
| tcctatatca ataccaatcg agtagcctgc attcttatta aaacaagca ttacaggtct | 1020 |
| tctgccgcct ctagattgcc ctgccccaat ttcaaaaata aatctttttt caagcagtgt | 1080 |
| atttacttga gaggagacag tagacttgtt taatcctgta atctcagaga gagttgccct | 1140 |
| ggagacaggg gagttcttca aaatttcatc taatattaat ttttgattca ttttttttac | 1200 |
| taaagcttga tctgcaattt gaataataac cactcctttg tttatccacc gaactaagtt | 1260 |
| ggtgtttttt gaagcttgaa ttagatattt aaaagtatca tatctaatat tataactaaa | 1320 |
| ttttctaaaa aaacattga aataaacatt tattttgtat atgatgagat aaagttagtt | 1380 |
| tattggataa acaaactaac tcaattaaga tagttgatgg ataaacttgt tcacttaaat | 1440 |
| caaaggggga aatgacaaat ggtccaaact agtgatatct aaaaatcaaa ggggggaaatg | 1500 |

<210> SEQ ID NO 13
<211> LENGTH: 846
<212> TYPE: DNA
<213> ORGANISM: Artificial Sequence
<220> FEATURE:
<223> OTHER INFORMATION: Synthetic DNA

<400> SEQUENCE: 13

| | |
|---|---|
| aaaaatcaaa gggggaaatg ggatccatta ccctgtctgc aggggcgctc gaggatgctc | 60 |
| aggggtttgc gaaggcgaca aaacgttatc cgcaaacgct tcagcagcat taccgcacat | 120 |
| tctgggaaca cgatatccct gtcgacgtca tcacgaaaga acaagacttt tcaccatata | 180 |
| aactgctgat cgtcccgatg ctgtatttaa tcagcgagga caccgttttcc cgtttaaaag | 240 |
| cgtttacggc tgacggcggc accttagtca tgacgtatat cagcggggtt gtgaatgagc | 300 |
| atgacttaac atacacaggc ggatggcatc cggatcttca agctatattt ggagttgagc | 360 |
| ctcttgaaac ggacaccctg tatccgaagg atcgaaacgc tgtcagctac cgcagccaaa | 420 |
| tatatgaaat gaaggattat gcaaccgtga ttgatgtaaa gacagcttca gtggaagcgg | 480 |
| tgtatcaaga agattttat gcgcgcacgc cagcggtcac aagccatgag tatcagcagg | 540 |
| gcaaggcgta ttttatcggc gcgcgtttgg aggatcaatt tcagcgtgat ttctatgagg | 600 |
| gtctgatcac agacctgtct ctctctccag ttttccggt tcggcacgga aaaggcgtct | 660 |
| ccgtacaagc gaggcaggat caggacaatg attatatttt tgtcatgaat ttcacggaag | 720 |

```
aaaaacagct ggtcacgttt gatcagagtg tgaaggacat aatgacagga gacatattgt      780
caggcgacct gacgatggaa aagtatgaag tgagaattgt cgtaaacaca cattaggggg      840
tacccc                                                                 846

<210> SEQ ID NO 14
<211> LENGTH: 59
<212> TYPE: DNA
<213> ORGANISM: Artificial Sequence
<220> FEATURE:
<223> OTHER INFORMATION: Synthetic DNA

<400> SEQUENCE: 14
tttctagctc taaaactggt ctaatgagga tcttcgacat ttattgtaca acacgagcc       59

<210> SEQ ID NO 15
<211> LENGTH: 33
<212> TYPE: DNA
<213> ORGANISM: Artificial Sequence
<220> FEATURE:
<223> OTHER INFORMATION: Synthetic DNA

<400> SEQUENCE: 15
gttttagagc tagaaatagc aagttaaaat aag                                   33

<210> SEQ ID NO 16
<211> LENGTH: 57
<212> TYPE: DNA
<213> ORGANISM: Artificial Sequence
<220> FEATURE:
<223> OTHER INFORMATION: Synthetic DNA

<400> SEQUENCE: 16
tctagctcta aaccgggaa tgaacgcagc agttacattt attgtacaac acgagcc          57

<210> SEQ ID NO 17
<211> LENGTH: 33
<212> TYPE: DNA
<213> ORGANISM: Artificial Sequence
<220> FEATURE:
<223> OTHER INFORMATION: Synthetic DNA

<400> SEQUENCE: 17
gttttagagc tagaaatagc aagttaaaat aag                                   33

<210> SEQ ID NO 18
<211> LENGTH: 59
<212> TYPE: DNA
<213> ORGANISM: Artificial Sequence
<220> FEATURE:
<223> OTHER INFORMATION: Synthetic DNA

<400> SEQUENCE: 18
tttctagctc taaaacatag tgagcttaca cctgagacat ttattgtaca acacgagcc       59
```

METHOD FOR PRODUCING N-ACETYLGLUCOSAMINE BY CO-UTILIZING GLUCOSE AND XYLOSE BASED ON CRISPRI

SEQUENCE LISTING

"Sequence Listing" recorded in computer readable form (CRF) as an appendix is submitted herewith and incorporated by reference in its entirety to the present application. The sequence listing information recorded in computer readable form is identical to the written (on paper or compact disc) sequence listing part of the disclosure as required by 37 CFR 1.821(f).

TECHNICAL FIELD

The present invention relates to a method for producing N-acetylglucosamine (GlcNAC) by co-utilizing glucose and xylose based on CRISPR interference (CRISPRi) and belongs to the field of genetic engineering.

BACKGROUND

GlcNAc is a monosaccharide in organisms and widely exists in bacteria, yeasts, molds, plants and animals. In human bodies, GlcNAc is a synthetic precursor of a glycosaminoglycan disaccharide unit and plays an important role in repair and maintenance of cartilage and joint tissue functions. Therefore, GlcNAc is widely used as a drug and a nutrient dietary additive to treat and repair joint damage. In addition, GlcNAc also has many applications in the field of cosmetics. At present, GlcNAc is mainly produced by acid hydrolysis of chitin in shrimp shells or crab shells, waste liquid produced by the method has relatively serious pollution to the environment, and a resulting product is prone to allergic reactions and not suitable for people who are allergic to seafood to take.

*Bacillus subtilis* is widely used as a production host for food enzyme preparations and important nutrient chemicals, and products thereof are certified by FDA as "generally regarded as safe" (GRAS) safety class. Therefore, adopting metabolic engineering methods to construct recombinant *Bacillus subtilis* is an effective way to produce food safe grade GlcNAc. However, the GlcNAc titer and yield on glucose of recombinant *Bacillus subtilis* (BSGNY-P$_{veg}$-glmS-P$_{43}$-GNA1) still cannot meet the requirements of industrialization, and therefore it is necessary to further increase the production capacity of the recombinant *Bacillus subtilis*. Glucose enters the glycolysis pathway and the pentose phosphate pathway after entering cells. At the same time, the synthesis of peptidoglycan also utilizes a part of glucose. In order to further increase the titer and yield of GlcNAc, it is necessary to reduce the flowing amount of glucose to these pathways. However, these pathways play an extremely important role in cell growth, and direct blocking these pathways inevitably affects cell growth. Therefore, these pathways need to be dynamically regulated and controlled to achieve a balance between cell growth and product synthesis. At the same time, xylose, serving as the main product of hydrolysis of lignocellulose, is the most abundant saccharide in nature except glucose, but most microorganisms have a weaker utilizing capacity on xylose, and the co-utilizing of glucose and xylose also has big problems. If a production strain which can efficiently co-utilize glucose and xylose is constructed, the production strain can utilize a renewable biomass resource for synthesis of a target product. In the previous work, the co-utilizing of glucose and xylose in the *B. subtilis* was achieved through the elimination of the regulation and control of xylose metabolism, that is, the expression of transport protein araE in the *B. subtilis* was enhanced and a xylose metabolism pathway gene xylAB from *Escherichia coli* was expressed (Reference literature: CHEN T et al. Engineering *Bacillus subtilis* for acetoin production from glucose and xylose mixtures [J]. Journal of Biotechnology, Elsevier B.V., 2013, 168(4): 499-505.). However, in their work, only the metabolism pathway of xylose was strengthened, and the metabolism of glucose was not regulated and controlled. When the cells can use both glucose and xylose, more glucose can be introduced into the synthesis pathway of the target product to avoid the waste of carbon resources.

SUMMARY

In order to solve the above problems, the present invention provides a method for efficiently producing GlcNAc by co-utilizing glucose and xylose based on CRISPRi.

A first objective of the present invention is to provide a genetically engineered bacterium capable of efficiently producing GlcNAc by co-utilizing glucose and xylose, wherein the glycolysis pathway, the pentose phosphate pathway and the peptidoglycan synthesis pathway of the genetically engineered bacterium were regulated by dCas9 protein and sgRNAs.

In an embodiment of the present invention, the genetically engineered bacterium uses *B. subtilis* as a host.

In an embodiment of the present invention, the genetically engineered bacterium integrates and expresses the dCas9 protein and simultaneously integrates three sgRNAs expression fragments targeting to zwf, pfkA and glmM respectively, encoding glucose 6-phosphate dehydrogenase, 6-phosphopfructokinase, and phosphoglucosamine mutase, respectively.

In an embodiment of the present invention, the amino acid sequence of the dCas9 protein is shown in SEQ ID NO: 1.

In an embodiment of the present invention, the nucleotide sequence of the sgRNA expression fragment targeting to zwf is shown in SEQ ID NO: 2; the nucleotide sequence of the sgRNA expression fragment targeting to pfkA is shown in SEQ ID NO: 3; the nucleotide sequence of the sgRNA expression fragment targeting to glmM is shown in SEQ ID NO: 4.

In an embodiment of the present invention, the dCas9 protein is integrated and expressed through a vector pLCx.

In an embodiment of the present invention, the sequence of the vector pLCx is shown in SEQ ID NO.5.

In an embodiment of the present invention, the sgRNA expression fragments are integrated into a genome of recombinant *B. subtilis* BSGNY-P$_{veg}$-glmS-P$_{43}$-GNA1.

In an embodiment of the present invention, the sgRNA expression fragments are integrated into amyE sites of the genome of the recombinant *B. subtilis* BSGNY-P$_{veg}$-glmS-P$_{43}$-GNA1.

A second objective of the present invention is to provide a method for constructing the genetically engineered bacterium, and the method uses the *B. subtilis* BSGNY-P$_{veg}$-glmS-P$_{43}$-GNA1 as an original strain; the original strain is based on *B. subtilis* 168 and obtained by modifying genotype as follows: ΔnagPΔgamPΔgamAΔnagAΔnagBΔldhΔptaΔglcKΔpckΔΔpyk::lox72, and express a phosphatase gene yqaB from *Escherichia coli* and glmS from the *B. subtilis* 168 regulated by a promoter $P_{veg}$, and the recombinant expression of GNA1 is regulated and controlled by a promoter $P_{43}$ on plasmid.

In an embodiment of the present invention, the integrated expression of the dCas9 protein is achieved by transforming a linearized vector pLCx-dCas9, and the amino acid sequence of dCas9 is shown in SEQ ID NO: 1.

In an embodiment of the present invention, the sequence of the integrated vector pLCx-dCas9 is shown in SEQ ID NO: 5, and the integrated vector pLCx-dCas9 is obtained by inserting dCas9 between restriction enzyme cutting sites BamHI and PstI of the integrated vector pLCx.

In an embodiment of the present invention, the sequence of the integrated vector pLCx is shown in SEQ ID NO: 6, and the integrated vector pLCx is constructed by one-step cloning of five fragments of F1, F2, F3, F4 and F5, wherein F1 contains a spectinomycin resistant gene aadA and an *Escherichia coli* replicon pMB1, F2 is 800 base fragments at the 5' end of the *B. subtilis* lacA gene, F3 is a chloramphenicol resistant fragment containing lox71 and lox66, F4 is xylose repressor protein and promoter, and F5 is 794 base fragments at the 3' end of the lacA gene. The xylose promoter of pLCx is followed by an RBS sequence of *B. subtilis* and followed by the two restriction enzyme cutting sites BamHI and PstI.

In an embodiment of the present invention, the integration of the three sgRNA expression fragments targeting to the zwf, pfkA and glmM genes respectively in the *B. subtilis* is obtained by transforming a linearized integrated vector psga-zpg.

In an embodiment of the present invention, the sequence of the integrated vector psga-zpg is shown in SEQ ID NO: 7, and the integrated vector psga-zpg is constructed by an integrated vector psga. The construction process is as follows: the construction of the integrated vectors psga-zwf, psga-pfkA and psga-glmM with sgRNA capable of acting on the pfkA, zwf and glmM genes is carried out by inverse PCR, and the three sgRNAs are assembled into the linearized psga vector using Golden Gate cloning.

In an embodiment of the present invention, the sequence of the integrated expression vector psga is shown in SEQ ID NO: 8, and the integrated expression vector psga consists of seven parts, namely spectinomycin resistant gene aadA, the *E. coli* replicon pMB1, 539 base fragments at the 5' end of a *B. subtilis* amyE gene, a bleomycin resistant fragment containing lox71 and lox66, the promoter $P_{veg}$, and the sgRNA fragments 1027 base fragments at the 3' end of the *B. subtilis* amyE gene. The construction process of psga is as follows: the amyE 3' fragments are inserted into restriction enzyme cutting sites EcoRI and HindIII of the vector pTargetF to obtain vector psga0; the amyE gene 5' fragments, the bleomycin resistant fragment containing lox71 and lox66 and the promoter $P_{veg}$ are assembled through fusion PCR and inserted between restriction enzyme cutting sites BamHI and BcuI of psga0. The sgRNA expression fragments can be integrated into the amyE sites of the genome of the *B. subtilis* by using the vector psga; the construction of the vector pTargetF is described in literature JIANG Y et al. Multigene editing in the *Escherichia coli* genome via the CRISPR-Cas9 system [J]. Applied and Environmental Microbiology, 2015, 81(7): 2506-2514.

A third objective of the present invention is to provide a method for efficiently producing GlcNAc by co-utilizing glucose and xylose. The method includes the following specific steps that the genetically engineered bacterium integrating and expressing the dCas9 protein and three sgRNA fragments targeting to genes zwf, pfkA and glmM is inoculated into a fermentation culture medium to produce GlcNAc.

In an embodiment of the present invention, the genetically engineered bacterium is a recombinant *B. subtilis*.

In an embodiment of the present invention, the fermentation culture medium contains glucose and xylose.

In an embodiment of the present invention, the fermentation culture medium contains a raw material which can be hydrolyzed to glucose and xylose.

In an embodiment of the present invention, according to the method, the recombinant *B. subtilis* is inoculated into a glucose-containing fermentation culture medium and xylose is added at a concentration of 5-20 g/L within 3-9 h.

A fourth objective of the present invention is to provide the application of the recombinant *B. subtilis* in drugs, nutraceuticals or cosmetics.

In an embodiment of the present invention, the application is the production of GlcNAc by using the recombinant *B. subtilis*.

In an embodiment of the present invention, the application includes activating a production strain, transferring the production strain to the fermentation culture medium with the inoculation amount of 5-10%, and culturing for 24-60 hours at the conditions of 35-38° C. and 150-250 rpm.

The present invention also provides the application of the genetic engineering bacterium in the fields of food, daily chemicals or preparation of drugs.

The present invention provides a method for efficiently co-utilizing glucose and xylose. Three major competitive pathways, namely, glycolysis pathway, pentose phosphate pathway and peptidoglycan synthesis pathway, for synthesis of GlcNAc in *B. subtilis* are dynamically regulated and controlled utilizing a CRISPRi system, that is, xylose is added in the logarithm middle and later periods of the fermentation for inducing the expression of dCas9 protein to inhibit the expression of genes zwf, pfkA and glmM in the *B. subtilis*, so that the amount of glucose in the synthesis pathways of GlcNAc is further increased, and at the same time, part of the added xylose is consumed, so that carbon sources needed for cell growth are supplemented, and the efficient co-utilizing of glucose and xylose by cells is achieved.

The constructed recombinant *B. subtilis* can efficiently synthesize GlcNAc through co-utilizing of glucose and xylose, the titer of GlcNAc can reach 20.5 g/L in a shake flask, and the yield of GlcNAc produced by fermentation is 0.612/g glucose. The increase of extracellular titer of GlcNAc in the recombinant *B. subtilis* is realized, and the foundation for further metabolic engineering transformation of the *B. subtilis* to produce GlcNAc and industrialization thereof is laid.

DETAILED DESCRIPTION

Figure 1:
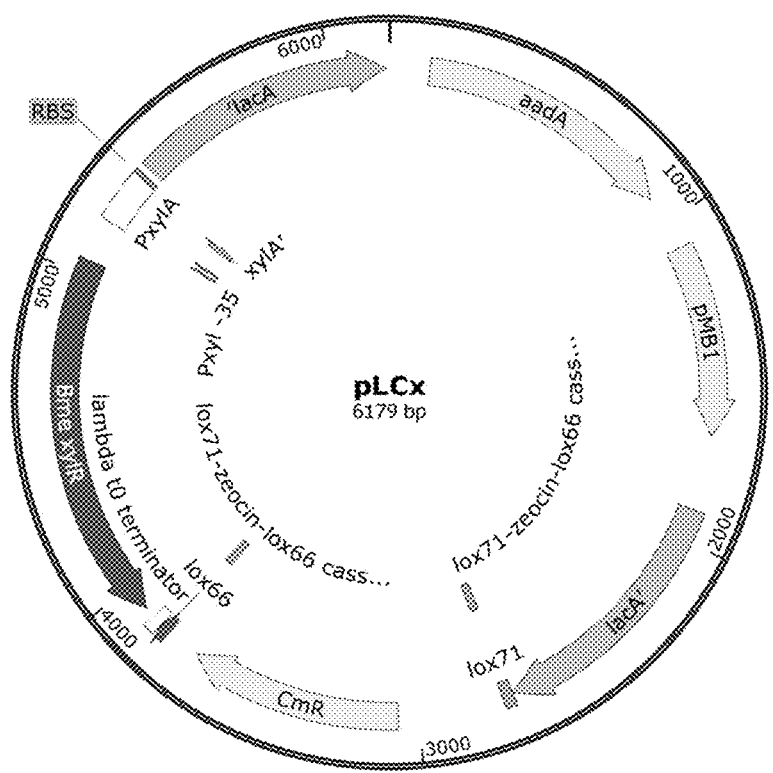
FIG. 1 shows the integrated expression vector pLCx.
Figure 2:
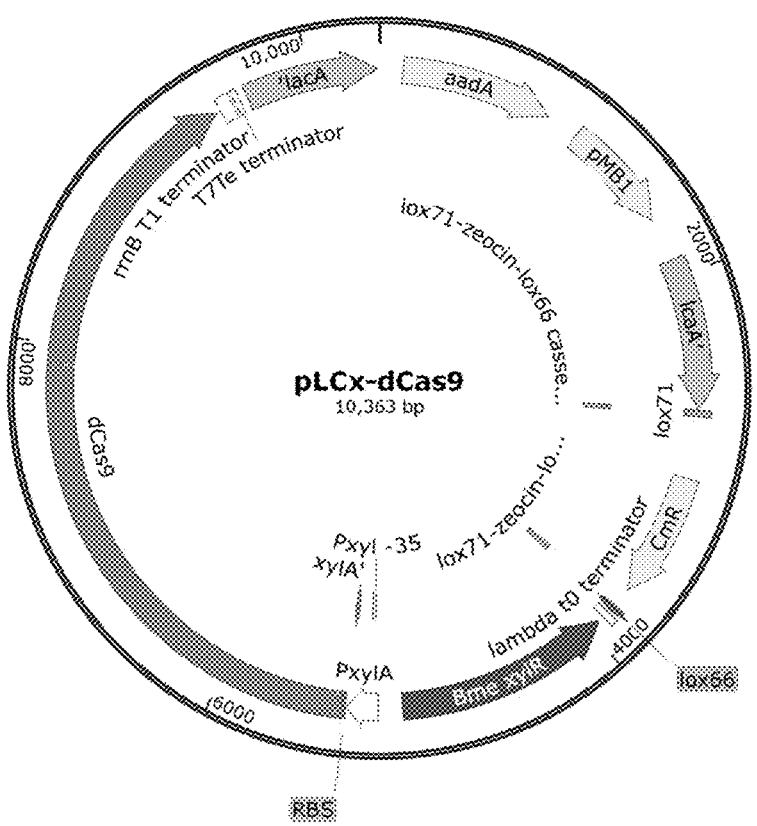
FIG. 2 shows the integrated expression vector pLCx-dCas9.
Figure 3:
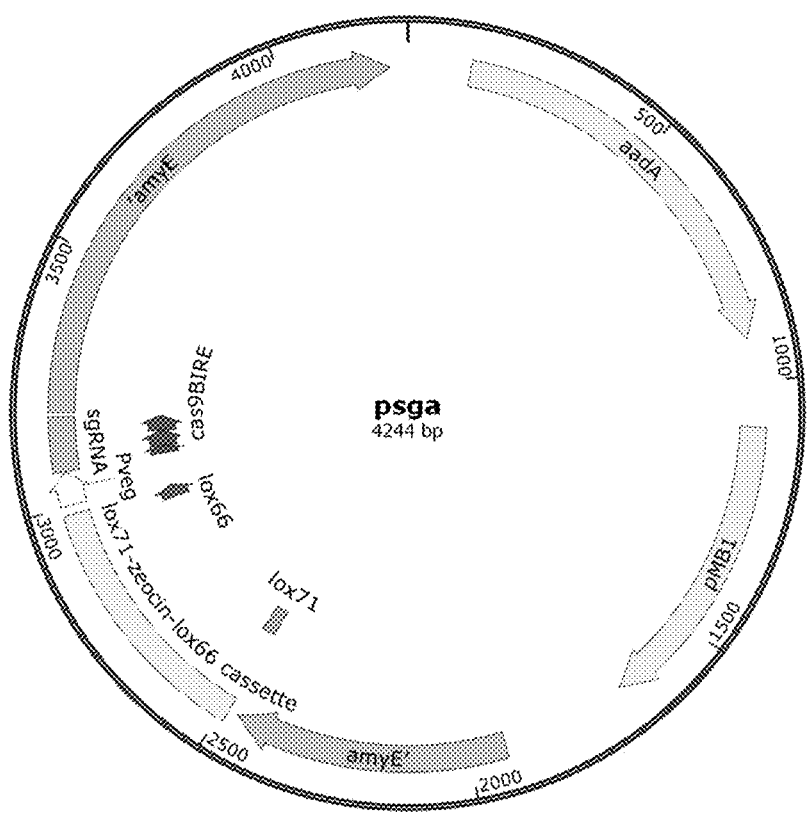
FIG. 3 shows the integrated expression vector psga.
Figure 4:
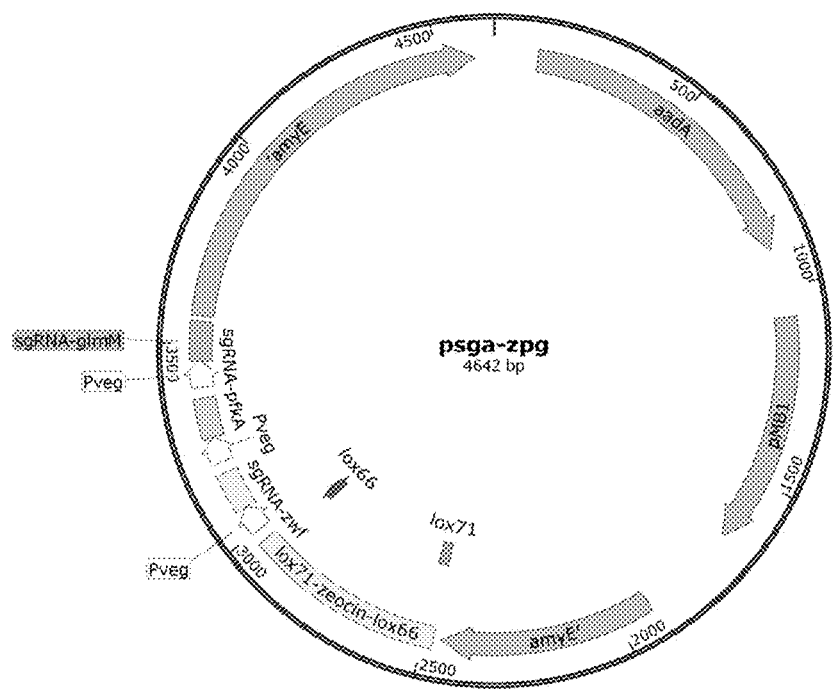
FIG. 4 shows the integrated expression vector psga-zpg.

Seed culture medium (g/L): tryptone 10, yeast powder 5, NaCl 10.

Fermentation culture medium (g/L): tryptone 6, yeast extract 12, $(NH_4)_2SO_4$ 6, $K_2HPO_4.3H_2O$ 12.5, $KH_2PO_4$ 2.5, $CaCO_3$ 5, trace elements 10 ml/L; a trace element solution contains (g/L): $MnSO_4.5H_2O$ 1.0, $CoCl_2.6H_2O$ 0.4, $NaMoO_4.2H_2O$ 0.2, $ZnSO_4.7H_2O$ 0.2, $AlCl_3.6H_2O$ 0.1, $CuCl_2H_2O$ 0.1, $H_3BO_4$ 0.05, and contains HCl 5M.

Determination method of GlcNAc: high performance liquid chromatography (HPLC) detection method: Agilent 1260, RID detector, HPX-87H column (Bio-Rad Hercules, Calif.), mobile phase: 5 mM $H_2SO_4$, flow rate: 0.6 mL/min, column temperature: 35° C., injection volume: 10 µL.

Calculation of yield of GlcNAc:

Yield of GlcNAc ($Y_{GlcNAc/Glc}$)=titer of GlcNAc (g/L)/consumed glucose (g/L).

Example 1: Construction of the CRISPRi System

A CRISPRi system constructed by the present invention consists of two integrated vectors, namely, pLCx-dCas9 (shown in SEQ ID NO: 5) and psga (shown in SEQ ID NO: 8). Wherein pLCx-dCas9 is used for integrating dCas9 protein induced and expressed by xylose into a lacA site of genome of B. subtilis, and psga can express and integrate sgRNA into an amyE site of the genome of the B. subtilis.

In a construction process of pLCx-dCas9, an integrated expression vector pLCx which can be used in the B. subtilis is first constructed, the integrated expression vector pLCx is constructed by one-step cloning of five fragments of F1, F2, F3, F4 and F5, and the sequences of F1 to F5 are shown in SEQ ID NO: 9 to SEQ ID NO: 13. F1 contains a spectinomycin resistant gene aadA and an E. coli replicon pMB1, F2 is 800 base fragments at the 5' end of B. subtilis lacA gene, F3 is a chloramphenicol resistant fragment containing lox71 and lox66, F4 is xylose repressor protein and a promoter, and F5 is 794 base fragments at the 3' end of the lacA gene. There are two restriction enzyme cutting sites BamHI and PstI behind RBS of pLCx for insertion of a target gene. After dCas9 is inserted between the restriction enzyme cutting sites BamHI and PstI of the integrated vector pLCx, the vector pLCx-dCas9 is obtained.

The vector psga consists of the spectinomycin resistant gene aadA, the E. coli replicon pMB1, 539 base fragments at the 5' end of a B. subtilis amyE gene, a bleomycin resistant fragment containing lox71 and lox66, a promoter $P_{veg}$, sgRNA fragments and 1027 base fragments at the 3' end of the B. subtilis amyE gene. The construction process is as follows: the amyE 3' fragments are inserted into restriction enzyme cutting sites EcoRI and HindIII of a vector pTargetF to obtain vector psga0; the 5' fragments of the amyE gene, the bleomycin resistant fragment containing lox71 and lox66 and the promoter $P_{veg}$ are assembled through fusion PCR and then inserted between restriction enzyme cutting sites BamHI and BcuI of psga0.

Example 2: Use of CRISPRi System to Regulate Expression of zwf, pfkA and glmM Primers are designed based on sequences of genes zwf, pfkA and glmM. Inverse PCR is carried out using vector psga as a template to obtain three vectors psga-zwf, psga-pfkA and psga-glmM which contain sgRNAs targeting to zwf, pfkA and glmM respectively, wherein the primers used by psga-zwf are sg-F: GTTTTAGAGCTAGAAATAG-CAAGTTAAAATAAG (SEQ ID NO: 15) and sg-zwf-R: TTTCTAGCTCTAAAACTGGTCTAATGAGGATCTTC-GACATTTATTGTACAACACGAGCC, (SEQ ID NO: 14) the primers used by psga-pfkA are sg-F: GTTTTA-GAGCTAGAAATAGCAAGTTAAAATAAG (SEQ ID NO: 15) and sg-pfkA-R: TCTAGCTCTAAAACCGGGAAT-GAACGCAGCAGTTACATTTATTGTACAACAC-GAGCC, (SEQ ID NO: 16) and the primers used by psga-glmM are sg-F: GTTTTAGAGCTAGAAATAG-CAAGTTAAAATAAG (SEQ ID NO: 15) and sg-glmM-R: TTTCTAGCTCTAAAACATAGTGAGCTTACACCT-GAGACATTTATTGTACAACACGAGCC (SEQ ID NO: 18).

The vectors psga-zwf, psga-pfkA, and psga-glmM are used as templates, and the three sgRNAs are assembled on a linearized psga vector using a Golden Gate assembly to obtain a vector psga-zpg containing these three sgRNAs simultaneously (The Golden Gate assembly method is described in literature ENGLER C et al. Golden gate shuffling: A one-pot DNA shuffling method based on type is restriction enzymes [J]. PLoS ONE, Public Library of Science, 2009, 4(5): e5553.).

The vectors pLCx-dCas9 and psga-zpg are linearized with a restriction endonuclease Eco91I and transformed into recombinant B. subtilis BSGNY-$P_{veg}$-glmS-$P_{43}$-GNA1 to obtain recombinant B. subtilis BSGNX-dCas9-zpg. By adding a certain amount of xylose in the fermentation culture medium of BSGNX-dCas9-zpg to induce the expression of dCas9, the expression of the zwf, pfkA and glmM can be regulated.

Example 3: Production of GlcNAc by Fermentation of Recombinant B. subtilis BSGNX-dCas9-zpg The recombinant B. subtilis constructed in the example 2 is used for fermentation in a shake flask. B. subtilis BSGNY-$P_{veg}$-glmS-$P_{43}$-GNA1 is used as a comparison and cultured and fermented under same conditions. Seeds cultured at 37° C. and 220 rpm for 12 hours are transferred into a fermentation culture medium at the inoculation amount of 5%, 15 g/L xylose is added to the culture medium at 6 hours after inoculation to obtain a mixture, and the mixture is cultured at 37° C. and 220 rpm for 48 hours. The content of GlcNAc in the final fermentation supernatant reaches 20.5 g/L, which is improved by 32.2% compared with that of the original strain (BSGNY-$P_{veg}$-glmS-$P_{43}$-GNA1). At the same time, the yield of GlcNAc obtained by fermentation of the recombinant Bacillus subtilis is 0.612 g/g glucose and is improved by 96.8% compared with that of the original strain (results are shown in Table 1), so that the increase in the extracellular titer and yield of GlcNAc in the recombinant B. subtilis is realized, at the same time, the efficient co-utilizing of glucose and xylose by the recombinant B. subtilis is achieved, and the foundation for further metabolic engineering transformation of the B. subtilis to produce GlcNAc and industrialization thereof is laid.

TABLE 1

| | Cell growth and GlcNAc synthesis before and after regulation by CRISPRi | | |
|---|---|---|---|
| Strains | GlcNAc Titer (g/L) | GlcNAc Yield (g/g) | Consumed xylose (g/L) |
| BSGNY-$P_{veg}$-glmS-$P_{43}$-GNA1 | 15.5 | 0.311 | 8.7 |
| BSGNX-dCas9-zpg | 20.5 | 0.612 | 12.5 |

Comparative Example 1: Influence of Xylose Addition Time on Cell Growth and GlcNAc Synthesis In the method of the present invention, xylose has two functions of (1) inducting expression of dCas9 protein, thereby reducing the expression of zwf, pfkA and glmM three genes, reducing the flowing amount of glucose in glycolysis pathway, pentose phosphate pathway and peptidoglycan synthesis pathway, and increasing glucose amount in GlcNAc synthesis pathway; (2) being used as a carbon source, absorbed and used by cells to supplement the carbon source required for cell growth after glucose metabolism is weakened. Therefore, the addition time of xylose determines the utilization of the two carbon sources of glucose and xylose by cells to a large extent.

Figure 5:
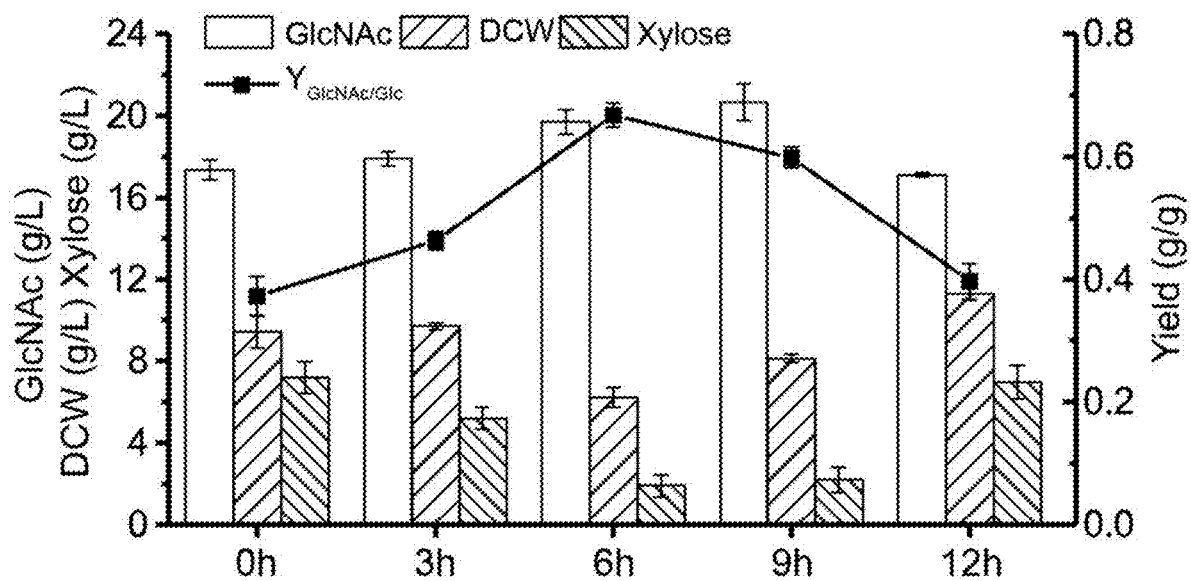
FIG. 5 shows the influence of xylose addition time on cell growth and GlcNAc synthesis.

Xylose having the final concentration of 15 g/L is added respectively at 0 h, 3 h, 6 h, 9 h and 12 h after inoculation, and fermentation results are shown in FIG. 5. The titer of GlcNAc reaches 20 g/L at 6 h and 9 h after inoculation. The yield of glucose is only 0.562 when xylose is added at 9 h, which is lower than 0.612 g/g when xylose is added at 6 h. The titer of GlcNAc and its yield on glucose are increased to various degrees and do not reach the optimal level when xylose is added at 0 h, 3 h and 12 h. Xylose needs to react with various intermediate metabolites in the pentose phosphate pathway when being used by cells. Early blocking of glucose utilization pathways can affect the accumulation of intermediate metabolites in the pentose phosphate pathway, and xylose cannot be used efficiently by the cells. When xylose is added too late, as the cells reach a stable period, at this time, the weakening of glucose utilization pathways has little promoting effect on the titer and yield of GlcNAc.

Figure 6:
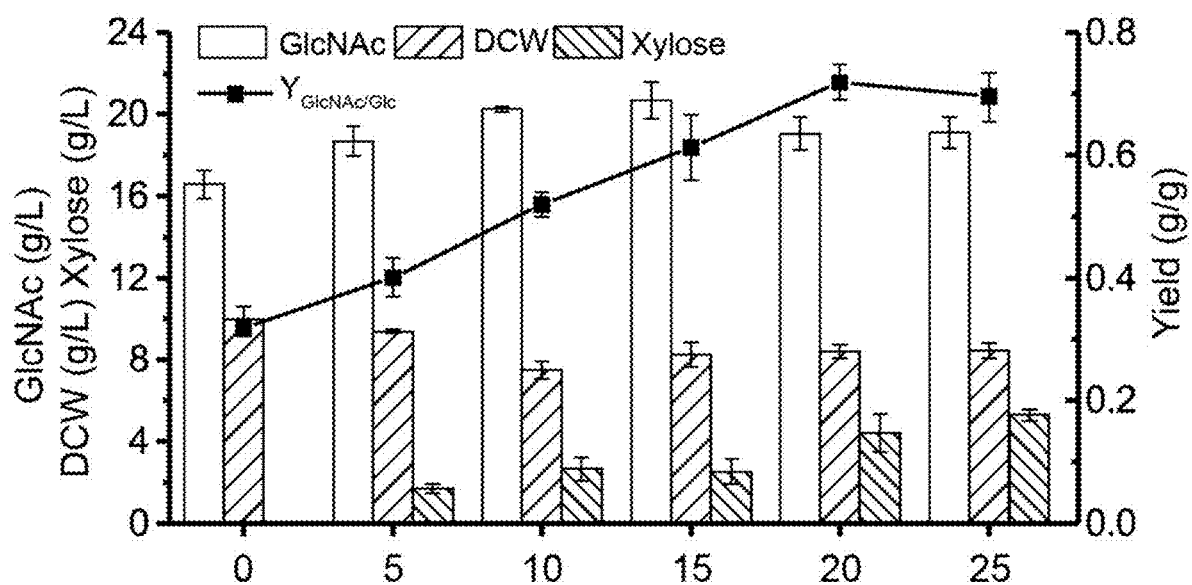
FIG. 6 shows the influence of xylose addition concentration on cell growth and GlcNAc synthesis.

Comparative Example 2: Influence of Xylose Addition Amount on Cell Growth and GlcNAc Synthesis The addition amount of xylose affects the expression level of dCas9 and therefore affects the expression level of the zwf, pfkA and glmM three genes; the change of the addition ratio of glucose and xylose also affects the utilization of the two carbon sources by the cells. Xylose is respectively added at 6 h after inoculation at the final concentrations of 0, 5, 10, 15, 20, and 25 g/L. Fermentation results are shown in FIG. 6. The titer of GlcNAc when 10 g/L and 15 g/L of xylose are added is 20.2 g/L and 20.5 g/L respectively, but the yield of GlcNAc is only 0.51 g/g when 10 g/L of xylose is added and is lower than 0.612 g/g when 15 g/L of xylose is added. The titer of GlcNAc when 0, 5, 20 and 25 g/L of xylose are added is 16.6, 18.6, 19.0 and 19.1 g/L respectively, which are all below 20 g/L. When the addition amount of xylose is too low, the inhibiting effect on the glucose utilization pathways is low, so that the promoting effect on GlcNAc synthesis is also limited; when the addition amount of xylose exceeds 15 g/L, though the yield of GlcNAc is further improved, at this time, the glucose utilization rate is lower, so that the titer of GlcNAc is not as high as that when 15 g/L of xylose is added.

What is claimed is:

1. A genetically engineered microorganism characterized by being capable of co-utilizing glucose and xylose to produce N-acetylglucosamine (GlcNAc); wherein the co-utilizing of glucose and xylose to produce GlcNAc is achieved by reducing the expression of at least one enzyme in each of the glycolysis pathway, pentose phosphor pathway and peptidoglycan synthesis pathway using a CRISPR interference (CRISPRi) system.

2. The genetically engineered microorganism according to claim 1, wherein the microorganism is a fungal cell or bacterial cell.

3. The genetically engineered microorganism according to claim 2, wherein the microorganism is a bacterial cell, wherein the bacterial cell integrates and expresses the gene encoding dCas9 protein and integrates three sgRNA expression fragments targeting to genes zwf, pfkA and glmM, respectively, encoding glucose 6-phosphate dehydrogenase, 6-phosphopfructokinase, and phosphoglucosamine mutase, respectively.

4. The genetically engineered microorganism according to claim 3, characterized in that the gene encoding dCas9 protein is integrated and expressed through a vector pLCx.

5. A method for constructing the genetically engineered microorganism according to claim 4, said method comprising transforming *Bacillus subtilis* to form an integrated gene encoding dCas9 protein through a vector pLCx-dCas9, and integrated sgRNA expression fragments targeting to the genes zwf, pfkA and glmM through a vector psga.

6. A method for producing produce N-acetylglucosamine (GlcNAc) by co-utilizing glucose and xylose, comprising inoculating the genetically engineered microorganism of claim 1 into a fermentation culture medium and fermenting the fermentation culture to produce GlcNAc.

7. The method according to claim 6, wherein a medium of the fermentation culture contains glucose and xylose, or contains a raw material which can be hydrolyzed to glucose and xylose.

8. The method according to claim 6, wherein the microorganism is *Bacillus subtilis*, wherein the *Bacillus subtilis* is innoculated into a glucose-containing fermentation culture medium and adding xylose at the concentration of 5-20 g/L within 3-9 hours.

9. The method according to claim 8, further comprising identifying a GlcNAc producing strain of said *Bacillus subtilis* and transferring the GlcNAc producing strain to the medium of the fermentation culture at the inoculation amount of 5-10%, and culturing at the conditions of 35-38° C. and 150-250 rpm for 24-60 h.

* * * * *